United States Patent
Lin et al.

(10) Patent No.: US 10,040,763 B2
(45) Date of Patent: Aug. 7, 2018

(54) ELECTROCHROMIC COMPOUNDS WITH IMPROVED COLOR STABILITY IN THEIR RADICAL STATES

(71) Applicant: Gentex Corporation, Zeeland, MI (US)

(72) Inventors: Rongguang Lin, Holland, MI (US); Kelvin L. Baumann, Holland, MI (US); Punam Giri, Holland, MI (US); Joel C. Nemes, Holland, MI (US); Leroy J. Kloeppner, Jenison, MI (US); David A. Theiste, Byron Center, MI (US)

(73) Assignee: GENTEX CORPORATION, Zeeland, MI (US)

( * ) Notice: Subject to any disclaimer, the term of this patent is extended or adjusted under 35 U.S.C. 154(b) by 59 days.

(21) Appl. No.: 15/040,946

(22) Filed: Feb. 10, 2016

(65) Prior Publication Data

US 2016/0229803 A1  Aug. 11, 2016

Related U.S. Application Data

(60) Provisional application No. 62/114,791, filed on Feb. 11, 2015.

(51) Int. Cl.
*C07D 213/04* (2006.01)
*C07D 213/22* (2006.01)
(Continued)

(52) U.S. Cl.
CPC ......... *C07D 213/22* (2013.01); *C07D 213/04* (2013.01); *C07F 9/581* (2013.01);
(Continued)

(58) Field of Classification Search
CPC ..... C07D 213/22; C07D 213/04; C07F 9/581; C07F 17/02; C08G 18/246;
(Continued)

(56) References Cited

U.S. PATENT DOCUMENTS 4,297,401 A   10/1981   Chern et al.
4,418,102 A   11/1983   Ferrato
(Continued)

FOREIGN PATENT DOCUMENTS

CN          102854688 A  *  1/2013
DE    10 2012 201 673 A1    8/2013
(Continued)

OTHER PUBLICATIONS

Lee et al., "γ-Cyclodextrin-Enhanced Dimerization of Viologen Radicals," Journal of Inclusion Phenomena and Molecular Recognition in Chemistry, vol. 26, 1996, pp. 219-232.
(Continued)

*Primary Examiner* — Daniel R Carcanague
(74) *Attorney, Agent, or Firm* — Foley & Lardner LLP; Bradley D. Johnson

(57) ABSTRACT

The invention relates to an electrochromic device and uses thereof, wherein the electrochromic device includes an electrochromic compound with reduced intermolecular interactions resulting in uncontrolled color changes represented by Formula (I):

$$[\text{structure of bipyridinium compound with substituents } R^1\text{-}R^{10}] \quad 2X^-$$

(I)

14 Claims, 8 Drawing Sheets

(51) Int. Cl.

| | | |
|---|---|---|
| *G02F 1/153* | (2006.01) | |
| *C07F 9/58* | (2006.01) | |
| *C08G 61/12* | (2006.01) | |
| *C07F 17/02* | (2006.01) | |
| *C08G 18/62* | (2006.01) | |
| *C08G 18/76* | (2006.01) | |
| *C08G 18/79* | (2006.01) | |
| *C08G 18/24* | (2006.01) | |
| *C09D 175/04* | (2006.01) | |
| *C08G 18/32* | (2006.01) | |
| *G02F 1/15* | (2006.01) | |

(52) U.S. Cl.
CPC ............ *C07F 17/02* (2013.01); *C08G 18/246* (2013.01); *C08G 18/3293* (2013.01); *C08G 18/6229* (2013.01); *C08G 18/7671* (2013.01); *C08G 18/792* (2013.01); *C09D 175/04* (2013.01); *G02F 1/15* (2013.01); *G02F 2001/1515* (2013.01)

(58) Field of Classification Search
CPC ............ C08G 18/3293; C08G 18/6229; C08G 18/7671; C08G 18/792; C09D 175/04; G02F 1/15; G02F 2001/1515
USPC .......................................................... 546/255
See application file for complete search history.

(56) References Cited

U.S. PATENT DOCUMENTS

| | | | | |
|---|---|---|---|---|
| 4,695,490 | A | | 9/1987 | McClelland et al. |
| 5,278,693 | A | * | 1/1994 | Theiste ................. G02F 1/1521 252/583 |
| 5,294,376 | A | * | 3/1994 | Byker .................. C07D 213/22 252/582 |
| 5,336,448 | A | * | 8/1994 | Byker ...................... C09K 9/02 252/583 |
| 5,596,023 | A | | 1/1997 | Tsubota et al. |
| 5,596,024 | A | | 1/1997 | Horie et al. |
| 5,888,431 | A | * | 3/1999 | Tonar ....................... C09K 9/02 252/583 |
| 6,020,987 | A | | 2/2000 | Baumann et al. |
| 6,037,471 | A | * | 3/2000 | Srinivasa ............. C07D 213/22 546/257 |
| 6,157,480 | A | | 12/2000 | Anderson et al. |
| 6,241,916 | B1 | | 6/2001 | Claussen et al. |
| 6,714,334 | B2 | | 3/2004 | Tonar |
| 7,372,611 | B2 | | 5/2008 | Tonar et al. |
| 2005/0231784 | A1 | | 10/2005 | Shinohara et al. |

FOREIGN PATENT DOCUMENTS

| | | | |
|---|---|---|---|
| DE | 102012201673 | * | 8/2013 |
| EP | 2 848 670 A1 | | 3/2015 |
| KR | 10-2012-0121305 A | | 10/2011 |
| KR | 10-2011-0108061 A | | 11/2015 |
| WO | WO2015040029 | * | 3/2015 |
| WO | WO2015040030 | * | 3/2015 |

OTHER PUBLICATIONS

Yasuda et al., "Electrochemical Behavior of Alkylviologen-cyclodextrin Inclusion Complexes. The Case of Non-alkyl Group Substituted Viologen," Journal of Applied Electrochmistry, vol. 18, 1988, pp. 333-338.

Yasuda et al., "Electrochromic Properties of Alkylviologen-cyclodextrin System," Journal of Applied Electrochmistry, vol. 17, issue 3, May 1987, pp. 567-573.

International Search Report and Written Opinion dated Aug. 19, 2016 in PCT/US2016/017402 (12 pages).

Kavanagh, Andrew, 'Stimuli responsive polymer gels for sensing applications', 2012, PhD thesis, Dublin City University. (232 pages).

Extended European Search Report for EP 16749826, dated Nov. 22, 2017 (7 pages).

\* cited by examiner

ELECTROCHROMIC COMPOUNDS WITH IMPROVED COLOR STABILITY IN THEIR RADICAL STATES

CROSS-REFERENCE TO RELATED APPLICATIONS

This application claims the benefit of priority to U.S. Provisional Patent Application No. 62/114,791, filed Feb. 11, 2015, the entire disclosure of which is hereby incorporated herein by reference in its entirety for any and all purposes.

FIELD

The present technology is generally related to electrochromic devices. More particularly, it is related to color stable viologens (e.g., 4,4'-bipyridinium-type salts), and electrochromic devices that incorporate them.

BACKGROUND

Devices which rely on an electrochromic switch mechanism, i.e. reversible color change in the presence of an applied electric field or current, have gained commercial importance. Viologens are one of the most commonly used electrochromic materials in such devices. Although viologen derivatives commonly used in electrochromic devices are known to provide intense colored radical states, variations in the local environment, such as reduced temperature or a change in solubility of the viologen derivatives, can result in an uncontrolled changes in the colored radical state. This is believed to be caused by intermolecular interactions of the viologen derivatives, commonly referred to as dimerization of the viologen. (See Yasuda et al., "Electrochromic Properties of Alkylviologen-cyclodextrin System," *J. Appl. Electrochem.* 17 (1987) 567-573; Yasuda et al., "Electrochemical Behavior of Alkylviologen-cyclodextrin Inclusion Complexes. The Case of Non-alkyl Group Substituted Viologen," *J. Appl. Electrochem.* 18 (1988) 333-338; Lee et al., "γ-Cyclodextrin-Enhanced Dimerization of Viologen Radicals," *J. Inclusion Phenomena and Molec. Recognition in Chem.*, 26 (1996) 219-232).

SUMMARY

In one aspect, an electrochemical device is provided, which includes a non-dimerizing electrochromic compound represented by Formula (I):

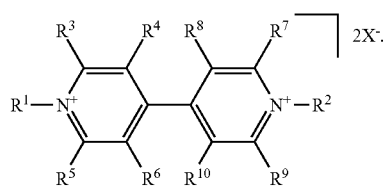

In Formula I, $R^1$ and $R^2$ are individually alkyl, siloxy alkyl, hydroxyalkyl, alkenyl, or aralkyl; $R^4$, $R^6$, $R^8$, and $R^{10}$ are individually H, $OR^{20}$, F, Cl, Br, I, CN, $NO_2$, alkyl, or aryl; $R^3$, $R^5$, $R^7$, and $R^9$ are individually H, OH, F, Cl, Br, I, CN, $NO_2$, alkyl, or aryl, $R^{20}$ is H or alkyl, and X is an anion. However, Formula (I) is subject to the proviso that $R^3$ and $R^5$, or $R^7$ and $R^9$, or $R^3$, $R^5$, $R^7$, and $R^9$ are individually secondary alkyl, tertiary alkyl, or aryl.

In one aspect, an electrochemical device is provided, which includes a non-dimerizing electrochromic compound represented by Formula (III):

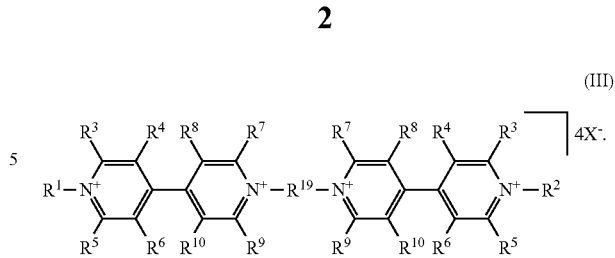

In Formula (III), $R^1$ and $R^2$ are individually alkyl, siloxyalkyl, hydroxyalkyl, alkenyl, or aralkyl; $R^4$, $R^6$, $R^8$, $R^{10}$ are individually H, $OR^{20}$, F, Cl, Br, I, CN, $NO_2$, alkyl, or aryl; $R^3$, $R^5$, $R^7$, and $R^9$ are individually H, OH, F, Cl, Br, I, CN, $NO_2$, alkyl, or aryl; $R^{19}$ is $(CH_2)_n$, or arylene, $R^{20}$ is H or alkyl, and n' is from 1 to 12; X is an anion; and wherein $R^3$, and $R^5$, or $R^7$, and $R^9$ are individually secondary alkyl, tertiary alkyl, or aryl.

In one embodiment, the non-dimerizing electrochromic compound is represented by Formula (IV)

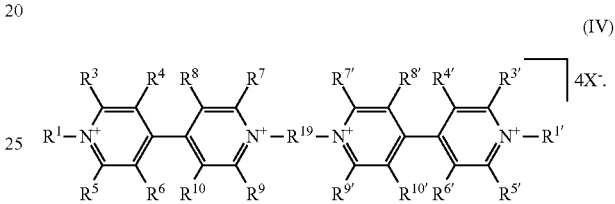

In Formula (IV), $R^1$ and $R^{1'}$ are individually alkyl, siloxyalkyl, hydroxyalkyl, alkylcarboxylate, alkylphosphonate, alkylisocyanate, carboxylate, phosphonate, isocyanate, alkenyl, or aralkyl; $R^4$, $R^6$, $R^8$, $R^{10}$, $R^{4'}$, $R^{6'}$, $R^{8'}$ and $R^{10'}$ are individually H, $OR^{20}$, F, Cl, Br, I, CN, $NO_2$, alkyl, or aryl; $R^7$, $R^9$, $R^{7'}$, and $R^{9'}$ are individually H, $OR^{20}$, F, Cl, Br, I, CN, $NO_2$, alkyl, or aryl; $R^{19}$ is $(CH_2)_{n'}$ or arylene, and n' is from 1 to 12; $R^{20}$ is H or alkyl, X is an anion; and either $R^3$, $R^5$, $R^{3'}$, and $R^{5'}$ are individually secondary alkyl, tertiary alkyl, or aryl; $R^7$, $R^9$, $R^{7'}$, and $R^{9'}$ are individually secondary alkyl, tertiary alkyl, or aryl. In some embodiments, for the non-dimerizing electrochromic compound represented by Formula (IV), $R^{19}$ is $(CH_2)_{n'}$ or arylene, and n' is from 1 to 12. In other embodiments, $R^1$ and $R^{1'}$ in Formula (IV) may be linkages within a polymer backbone. Accordingly, the compound of Formula (IV) may be a monomeric unit in a polymer backbone.

In one embodiment, the non-dimerizing electrochromic compound is represented by Formula (V)

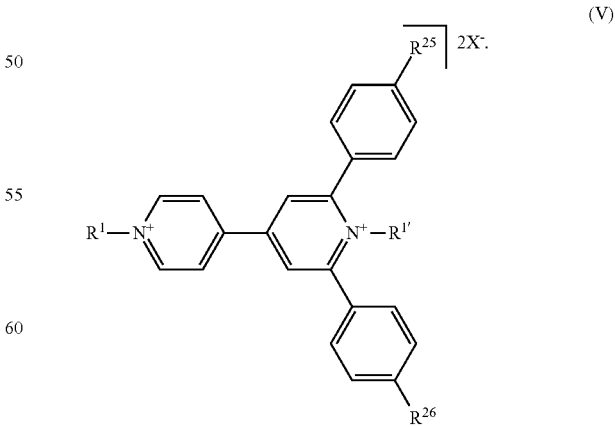

In Formula V, $R^1$ and $R^{1'}$ are individually $-(CH_2)_nOH$, $-(CH_2)_nBr$, $-(CH_2)_nCl$, $-(CH_2)_nSi(OH)_3$, $-(CH_2)_nSi(OMe)_3$, $-(CH_2)_nSi(OEt)_3$,

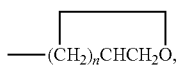
—(CH$_2$)$_n$CHCH$_2$O,

—(CH$_2$)$_n$CH═CH$_2$, —(CH$_2$)$_n$COC(O)CH═CH$_2$, or —(CH$_2$)$_n$COC(O)C(CH$_3$)═CH$_2$; R$^{25}$ and R$^{26}$ are individually H, Me, Et, Pr, OMe, OEt, OPr, OC(O)(CH$_2$)$_n$Si(OH)$_3$, OC(O)(CH$_2$)$_n$Si(OMe)$_3$, OC(O)NH(CH$_2$)$_n$Si(OEt)$_3$, OC(O)NH(CH$_2$)$_n$COOH, OC(O)NH(CH$_2$)$_n$P(O)(OH)$_2$, or OC(O)NH(CH$_2$)$_n$NCO; n is 1 to 12; and X is an anion.

In some embodiments, the device exhibits a $\lambda_{max}$ of greater than about 580 nm. In some embodiments, the device exhibits a $\lambda_{max}$ of greater than about 600 nm. In some embodiments, the device is an electrochromic window or an electrochromic mirror.

DETAILED DESCRIPTION

Figure 1:
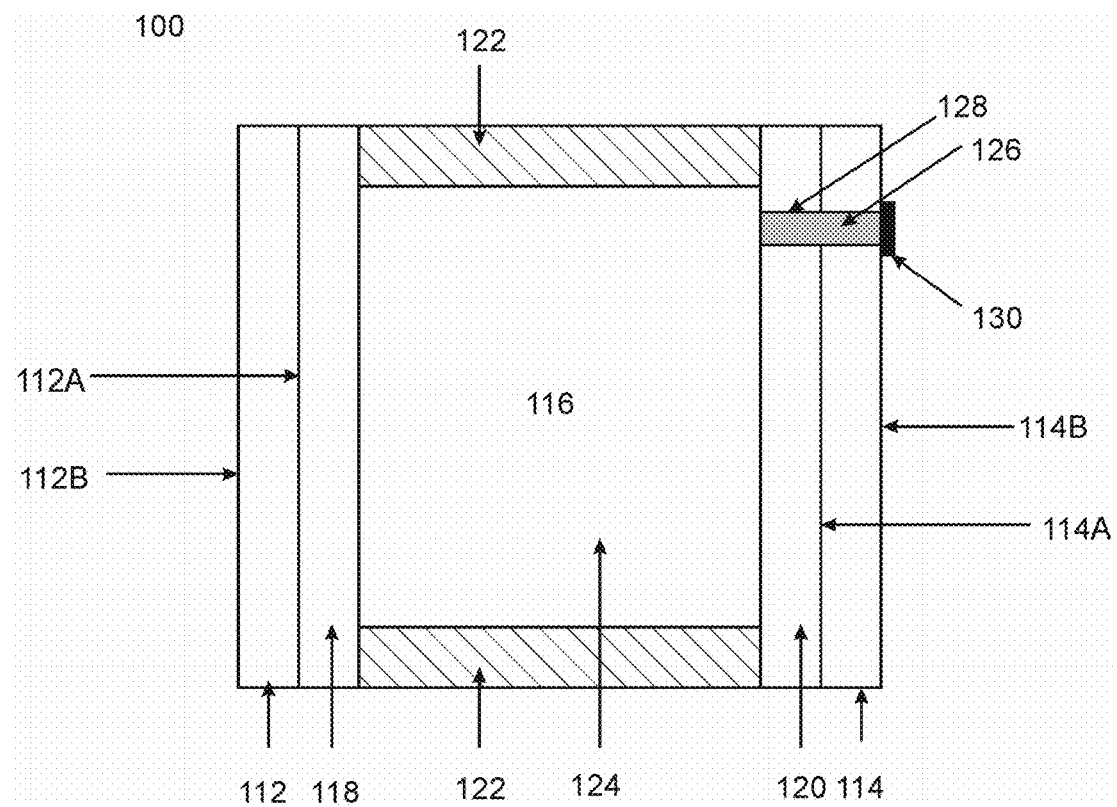
FIG. 1 is a cross-sectional schematic representation of an electrochromic device, according to one embodiment.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be constructed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Such substitution includes solubility enhancing groups as described in U.S. Pat. No. 6,445,486.

As used herein, $C_m$-$C_n$, such as $C_1$-$C_{12}$, $C_1$-$C_8$, or $C_1$-$C_6$ when used before a group refers to that group containing m to n carbon atoms.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=$CH_2$, C=$CH_2$, or C=CHCH$_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

"TFSI" as used herein refers to bis(trifluoromethanesulfonyl)imide, as illustrated below:

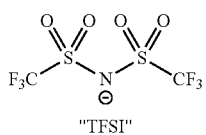

"TFSI"

In one aspect, non-dimerizing electrochromic compounds are provided. Illustrative non-dimerizing electrochromic compounds include those that may be represented by Formula (I):

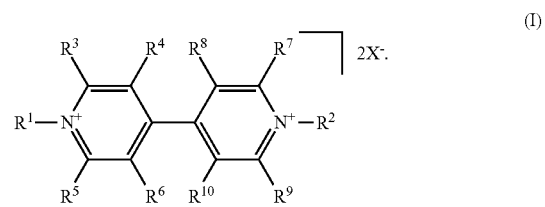

In Formula (I), $R^1$ and $R^2$ may be individually alkyl, siloxyalkyl, hydroxyalkyl, carboxyalkyl, phosphonylalkyl, alkenyl, or aralkyl; $R^4$, $R^6$, $R^8$, and $R^{10}$ may be individually H, $OR^{20}$, F, Cl, Br, I, CN, $NO_2$, alkyl, or aryl; $R^{20}$ is H or alkyl; and X is an anion. Also in Formula I, $R^3$, $R^5$, $R^7$, and $R^9$ may individually be H, OH, F, Cl, Br, I, CN, $NO_2$, alkyl, or aryl. The compound of Formula I may be subject to the following two provisos. At least, $R^3$ and $R^5$ or $R^7$ and $R^9$, are individually secondary alkyl, tertiary alkyl, or aryl. Further, when $R^1$ and $R^2$ are each methyl, $R^3$ and $R^5$, or $R^7$ and $R^9$ are not phenyl or phenyl substituted with methyl. In some embodiments, $R^1$ and/or $R^2$ are links to a polymer backbone, such that the viologen is tied into the polymer backbone, or $R^1$ and/or $R^2$ are bridging groups between other Formula I compounds. As discussed previously in defining the terms, the alkyl, siloxyalkyl, hydroxyalkyl, carboxyalkyl, phosphonylalkyl, alkenyl, or aralkyl of $R^1$ and $R^2$ may be substituted or unsubstituted. Substitution may include solubilizing groups such as ammonium groups, phosphonium groups, pyridinium groups, or other solubility enhancing groups as described in U.S. Pat. No. 6,445,486. When the $R^1$ and $R^2$ of Formula (I) are substituted with such solubilizing groups, it may be $R^4$, $R^6$, $R^8$, and $R^{10}$ are H.

X is an anion that may be, but is not limited to, a halide, a borate, a fluoroborate, a tetraaryl borate, a hexafluoro metal or metalloid, a sulfate, a sulfonate, a sulfonamide, a carboxylate, a perchlorate, a tetrachloroferrate, or the like. Illustrative X groups include, but are not limited to: $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $N(CF_3SO_2)_2^-$, $C(CF_3SO_2)_3^-$, $N(SO_2C_2F_5)_2^-$, $^-Al(OC(CF_3)_3)_4$ or $^-BAr_4$, wherein Ar is a aryl or fluorinated aryl group. In one embodiment, $X^-$ is $^-BAr_4$ and Ar is a pentafluorophenyl group. In some embodiments, X is a tetrafluoroborate or a bis(trifluoromethylsulfonyl) imide anion. When shown in any compound herein multiple X's may be a mixture of two or more such anions.

$R^1$ and $R^2$ may be individually a $C_1$-$C_{12}$ alkyl group that is substituted or unsubstituted, or which may be further connected to an aryl group, cyclic group, heterocyclic group, or heteroaryl group. In some embodiments, $R^1$ and $R^2$ are individually a $C_1$-$C_{12}$ alkyl group substituted with a silyloxy or a hydroxyl group at the end. In some embodiments, $R^1$ and $R^2$ are individually a hydroxyalkyl group. In some embodiments, $R^1$ is a hydroxypentanyl group. In some embodiments, $R^2$ is a hydroxyundecanyl group.

$R^4$, $R^6$, $R^8$, and $R^{10}$ may be individually H, OH, or alkyl. In some embodiments, $R^4$, $R^6$, $R^8$, and $R^{10}$ are individually H. In some embodiments, $R^4$, $R^6$, $R^8$, and $R^{10}$ are individually $C_1$-$C_6$ alkyl. In some embodiments, $R^4$, $R^6$, $R^8$, and $R^{10}$ are all H.

$R^3$, $R^5$, $R^7$, and $R^9$ may be individually H, alkyl, or aryl, with the proviso that $R^3$ and $R^5$, or $R^7$ and $R^9$, or $R^3$ and $R^5$ and $R^7$ and $R^9$ are individually secondary alkyl, tertiary alkyl, or aryl. In some embodiments, $R^3$, $R^5$, $R^7$, and $R^9$ are individually secondary or tertiary $C_3$-$C_{12}$ alkyl. In some embodiments, $R^3$, $R^5$, $R^7$, and $R^9$ are individually H or aryl.

In some embodiments, $R^3$ and $R^5$ are individually secondary alkyl, tertiary alkyl, or aryl. In some embodiments, $R^3$ and $R^5$ are individually aryl. In some embodiments, $R^3$ and $R^5$ are aryl and $R^7$ and $R^9$ are H.

In the above embodiments, $R^3$, $R^5$, $R^7$, or $R^9$ may be an aryl group of Formula (II):

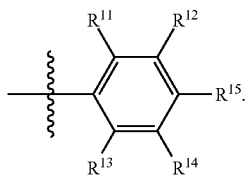

(II)

In Formula (II), $R^{11}$, $R^{12}$, $R^{13}$, and $R^{14}$ may be individually H, $OR^{20}$, F, Cl, Br, I, CN, $NO_2$, or alkyl; $R^{15}$ is H, OH, F, Cl, Br, I, CN, $NO_2$, —OC(O)$NR^{16}R^{17}$, alkyl, or alkoxy; $R^{16}$ is H or alkyl; $R^{20}$ is H or alkyl; and $R^{17}$ is H, alkyl or siloxy alkyl.

In some embodiments, in Formula (II), $R^{11}$, $R^{12}$, $R^{13}$, and $R^{14}$ may be individually H or alkyl. In some embodiments, $R^{11}$, $R^{12}$, $R^{13}$, and $R^{14}$ are individually H or $C_1$-$C_6$ alkyl. In some embodiments, $R^{11}$, $R^{12}$, $R^{13}$, and $R^{14}$ are all H. In some embodiments, $R^{15}$ is H, OH, alkyl, or alkoxy. In some embodiments, $R^{15}$ is $C_1$-$C_6$ alkyl. In some embodiments, $R^{15}$ is H, methyl, ethyl, propyl, iso-propyl, butyl, sec-butyl, or tert-butyl. In some embodiments, $R^{11}$, $R^{12}$, $R^{13}$, and $R^{14}$ are H, and $R^{15}$ is H, methyl, ethyl, propyl, iso-propyl, butyl, sec-butyl, or tert-butyl. In some embodiments, $R^{16}$ is H. In other embodiments, $R^{16}$ is $C_1$-$C_6$ alkyl. In some embodiments, $R^{17}$ is alkyl or siloxy alkyl. In some embodiments, $R^{17}$ is H, methyl, ethyl, propyl, iso-propyl, butyl, sec-butyl, tert-butyl, or —$(CH_2)_n Si(OR^{18})_3$, $R^{18}$ H or alkyl, and n is 1 to 10.

Alternatively in Formula (I), $R^1$ and $R^2$ may be individually alkyl or hydroxyalkyl, and $R^3$ and $R^5$, or $R^7$ and $R^9$, may be individually an aryl of Formula (II). In some embodiments, $R^3$ and $R^5$ are an aryl group. In some embodiments, $R^7$ and $R^9$ are an aryl group. In some embodiments, $R^3$ and $R^5$, or $R^7$ and $R^9$, are a phenyl. In some embodiments, $R^3$, $R^5$, $R^3$ and $R^9$ are each an aryl group of Formula (II). In some embodiments, $R^{11}$, $R^{12}$, $R^{13}$, and $R^{14}$ are H, and $R^{15}$ is H, OH, alkyl or alkoxy. In some embodiments, $R^{11}$, $R^{12}$, $R^{13}$, and $R^{14}$ are H, and $R^{15}$ is H, OH, Me, or methoxy.

In one embodiment, for a compound of Formula (I), $R^1$ and $R^2$ are individually an alkyl group, and $R^3$ and $R^5$, or $R^7$ and $R^9$, are individually aryl of Formula (II). In some embodiments, $R^3$ and $R^5$, or $R^7$ and $R^9$, may be substituted phenyl. In some embodiments, $R^3$ and $R^5$, or $R^7$ and $R^9$, may be phenyl substituted with a carbamate group. In some embodiments, $R^3$ and $R^5$, is each an aryl of Formula (II). In other embodiments, $R^7$ and $R^9$, may each be an aryl of Formula (II). In some embodiments, $R^{11}$, $R^{12}$, $R^{13}$, and $R^{14}$ are H, and $R^{15}$ is —OC(O)$NR^{16}R^{17}$. In some embodiments, $R^{16}$ is H. In some embodiments, $R^{17}$ is alkyl or siloxy alkyl. In some embodiments, $R^{17}$ is —$(CH_2)_n Si(OR^{18})_3$, $R^{18}$ H or alkyl, and n is 1 to 10. In some embodiments, $R^{17}$ is —$(CH_2)_n Si(OR^{18})_3$, $R^{18}$ is methyl or ethyl, and n is 3.

In some embodiments, $R^1$ and/or $R^2$ are sterically hindered groups such as, but not limited to, isobutyl, ethylhexyl, neopentyl, and the like. Bridged compounds of Formula I include, but are not limited to:

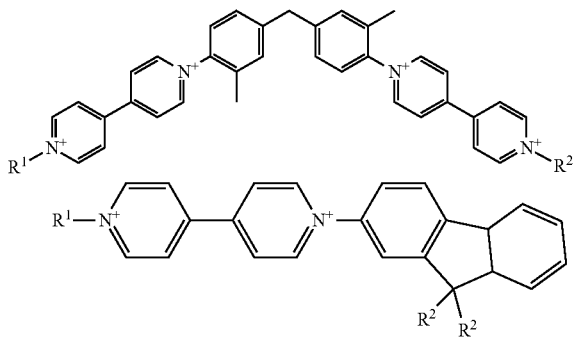

In one aspect, the non-dimerizing electrochromic compound is represented by Formula (III)

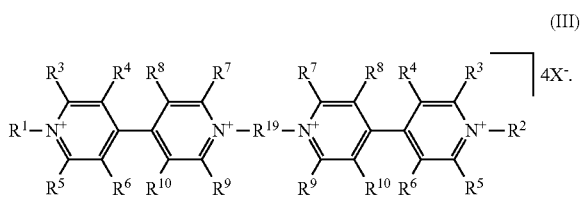

(III)

In Formula (III), $R^{19}$ is $(CH_2)_{n'}$ or arylene, and n' is from 1 to 12.

For compounds of Formula (III), $R^1$, $R^3$-$R^{10}$, and X are as defined herein for Formula (I). In some embodiments, $R^{19}$ is $(CH_2)_{n'}$ wherein n' is from 1-10. In some embodiments, $R^{19}$ is $(CH_2)_{3-8}$. In other embodiments, $R^{19}$ is phenylene. In some embodiments, $R^{19}$ is 1,4-phenylene.

Alternatively in Formula (I), $R^1$ and $R^2$ may be individually alkyl or hydroxyalkyl, and $R^3$ and $R^5$, or $R^7$ and $R^9$, may be individually an aryl of Formula (II). In some embodiments, $R^3$ and $R^5$ are an aryl group. In some embodiments, $R^7$ and $R^9$ are an aryl group. In some embodiments, $R^{11}$, $R^{12}$, $R^{13}$, and $R^{14}$ are H, and $R^{15}$ is H, OH, alkyl, or alkoxy. In some embodiments, $R^{11}$, $R^{12}$, $R^{13}$, and $R^{14}$ are H, and $R^{15}$ is methyl. In some embodiments, $R^{11}$, $R^{12}$, $R^{13}$, and $R^{14}$ are H, and $R^{15}$ is H, OH, Me, or methoxy. In some embodiments, $R^{19}$ is $(CH_2)_{n'}$ wherein n' is from 1-10. In some embodiments, $R^{19}$ is 1,4-phenylene.

In some embodiments, for a compound of Formula (I), $R^1$ and $R^2$ are individually methyl, $R^3$ and $R^5$ are each an aryl of Formula (II), $R^{11}$, $R^{12}$, $R^{13}$, and $R^{14}$ are H, $R^{15}$ is H, OH, Me, or methoxy, and $R^{19}$ is $(CH_2)_{n'}$ wherein n' is from 1-10.

In some embodiments, for a compound of Formula (I), $R^1$ and $R^2$ are individually alkyl or hydroxyalkyl, $R^7$ and $R^9$ are each an aryl of Formula (II), $R^{11}$, $R^{12}$, $R^{13}$, and $R^{14}$ are H, and $R^{15}$ is methyl, and $R^{19}$ is 1,4-phenylene.

In some embodiments, for a compound of Formula (I), $R^1$ and $R^2$ are individually alkyl or hydroxyalkyl, $R^7$ and $R^9$ are each an aryl of Formula (II), $R^{11}$, $R^{12}$, $R^{13}$, and $R^{14}$ are H, and $R^{15}$ is methyl, and $R^{19}$ is $(CH_2)_{n'}$ wherein n' is 3.

In another aspect, the non-dimerizing electrochromic compound is represented by Formula (IV)

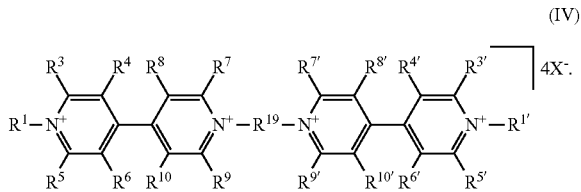

(IV)

In Formula (IV), $R^1$ and $R^{1'}$ may be individually alkyl, siloxyalkyl, hydroxyalkyl, alkylcarboxylate, alkylphosphonate, alkylisocyanate, carboxylate, phosphonate, isocyanate, alkenyl, or aralkyl; $R^4$, $R^6$, $R^8$, $R^{10}$, $R^{4'}$, $R^{6'}$, $R^{8'}$ and $R^{10'}$ may be individually H, $OR^{20}$, F, Cl, Br, I, CN, $NO_2$, alkyl, or aryl; and $R^3$, $R^5$, $R^7$, $R^9$, $R^{3'}$, $R^{5'}$, $R^{7'}$, and $R^{9'}$ may be individually H, $OR^{20}$, F, Cl, Br, I, CN, $NO_2$, alkyl, or aryl, with the proviso that $R^3$, $R^5$, $R^{3'}$, and $R^{5'}$ are individually secondary alkyl, tertiary alkyl, or aryl; and $R^{19}$ is $(CH_2)_{n'}$ or arylene, $R^{20}$ is H or alkyl, and $n'$ is from 1 to 12. X is an anion as defined above.

The compound of Formula (IV) includes where $R^1$ and $R^{1'}$ may be individually alkyl, siloxyalkyl, hydroxyalkyl, alkylcarboxylate, alkylphosphonate, alkylisocyanate, alkenyl, or aralkyl; $R^4$, $R^6$, $R^8$, $R^{10}$, $R^{4'}$, $R^{6'}$, $R^{8'}$ and $R^{10'}$ may be individually H, OH, F, Cl, Br, I, CN, $NO_2$, alkyl, or aryl; and $R^3$, $R^5$, $R^7$, $R^9$, $R^{3'}$, $R^{5'}$, $R^{7'}$, and $R^{9'}$ may be individually H, OH, F, Cl, Br, I, CN, $NO_2$, alkyl, or aryl, with the proviso that $R^7$, $R^9$, $R^{7'}$, and $R^{9'}$ are individually secondary alkyl, tertiary alkyl, or aryl; $R^{19}$ is $(CH_2)_{n'}$ or arylene, and $n'$ is from 1 to 12. X is an anion as defined above.

In another aspect, the non-dimerizing electrochromic compound is represented by Formula (V)

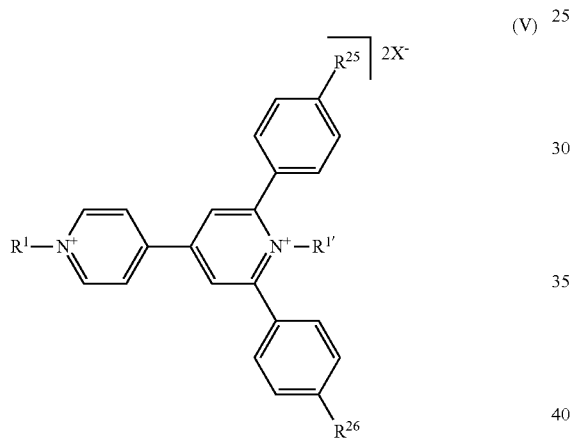

In Formula (V), $R^1$ and $R^{1'}$ are individually —$(CH_2)_n$OH, —$(CH_2)_n$Br, —$(CH_2)_n$Cl, —$(CH_2)_n$Si(OH)$_3$, —$(CH_2)_n$Si(OMe)$_3$, —$(CH_2)_n$Si(OEt)$_3$,

—$(CH_2)_n$CH=CH$_2$, —$(CH_2)_n$COC(O)CH=CH$_2$, or —$(CH_2)_n$COC(O)C(CH$_3$)=CH$_2$; $R^{25}$ and $R^{26}$ are individually H, Me, Et, Pr, OMe, OEt, OPr, OC(O)(CH$_2$)$_n$Si(OH)$_3$, OC(O)(CH$_2$)$_n$Si(OMe)$_3$, OC(O)NH(CH$_2$)$_n$Si(OEt)$_3$, OC(O)NH(CH$_2$)$_n$COOH, OC(O)NH(CH$_2$)$_n$P(O)(OH)$_2$, or OC(O)NH(CH$_2$)$_n$NCO; and n is 1 to 12.

In some embodiments, for compounds of Formula (V), $R^1$ and $R^{1'}$ are individually —$(CH_2)_n$OH, —$(CH_2)_n$Si(OH)$_3$, —$(CH_2)_n$Si(OMe)$_3$, —$(CH_2)_n$Si(OEt)$_3$,

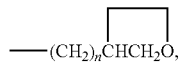

—$(CH_2)_n$CH=CH$_2$, —$(CH_2)_n$COC(O)CH=CH$_2$, or —$(CH_2)_n$COC(O)C(CH$_3$)=CH$_2$. In some embodiments, for compounds of Formula (V), $R^1$ and $R^{1'}$ are each —$(CH_2)_n$OH, wherein n=1 to 15. In some embodiments, for compounds of Formula (V), $R^{25}$ and $R^{26}$ are each OC(O)NH(CH$_2$)$_n$Si(OEt)$_3$; and n is 1 to 12.

In some embodiments, a compound is provided, wherein the compound is:

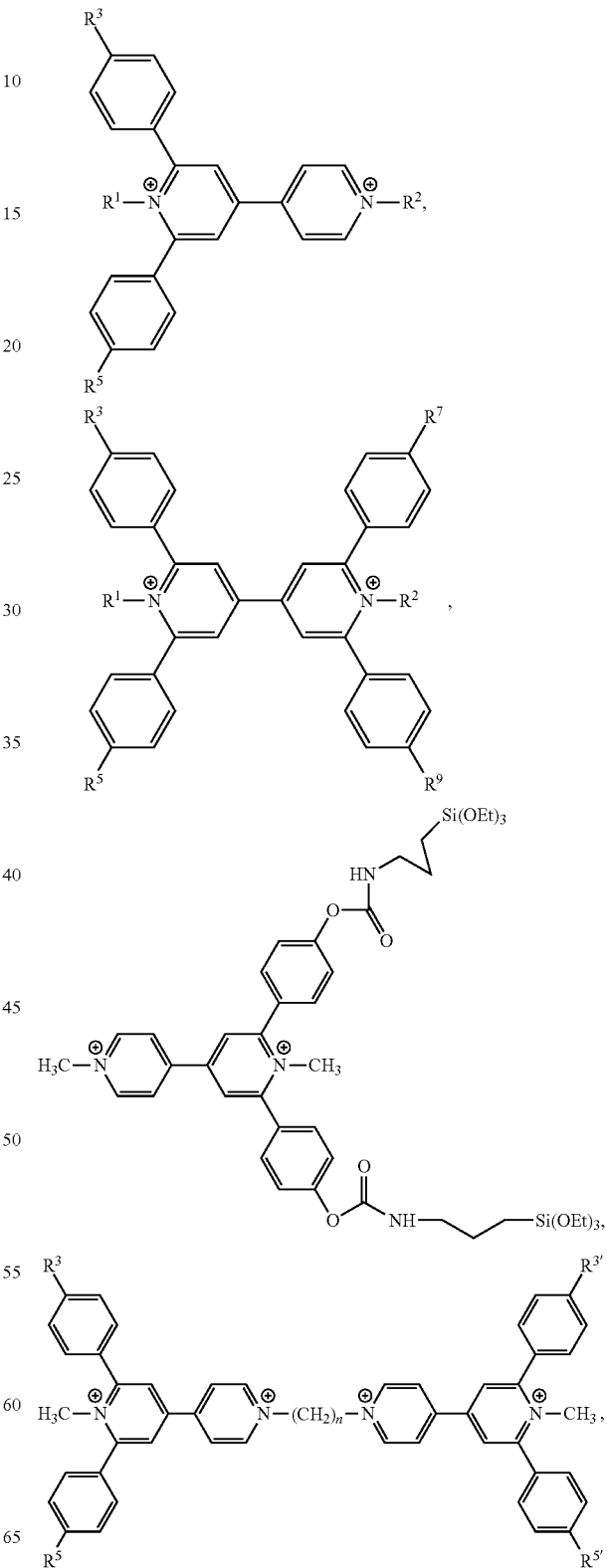

-continued

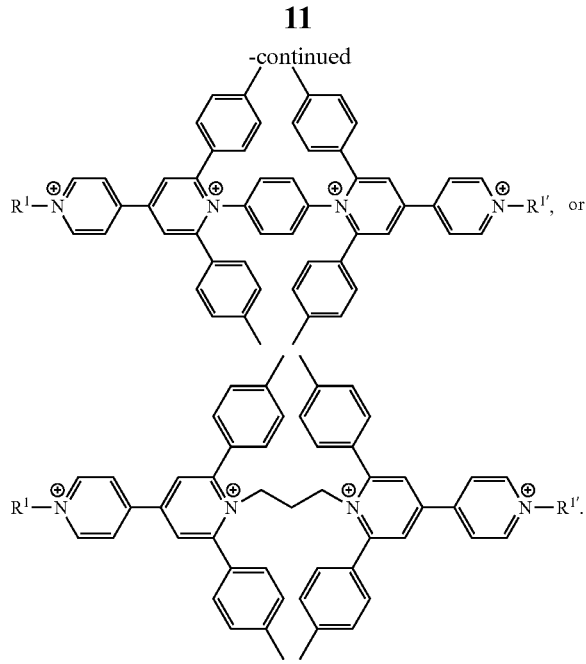

In another aspect, electrochemical devices are provided incorporating non-dimerizing viologen materials. In some embodiments, an electrochemical device is provided, which includes a non-dimerizing electrochromic compound represented by Formula (I):

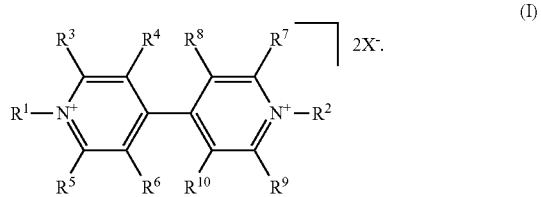
(I)

In Formula (I), $R^1$ and $R^2$ are individually alkyl, siloxy alkyl, hydroxyalkyl, alkenyl, or aralkyl; $R^4$, $R^6$, $R^8$, and $R^{10}$ are individually H, $OR^{20}$, F, Cl, Br, I, CN, $NO_2$, alkyl, or aryl; $R^{20}$ is H or alkyl; and X is an anion. In Formula (I), $R^3$, $R^5$, $R^7$, and $R^9$ are individually H, OH, F, Cl, Br, I, CN, $NO_2$, alkyl, or aryl, with the proviso that either $R^3$ and $R^5$, or $R^7$ and $R^9$, or $R^3$, $R^5$, $R^7$, and $R^9$ are individually secondary alkyl, tertiary alkyl, or aryl. As discussed previously in defining the terms, the alkyl, siloxyalkyl, hydroxyalkyl, carboxyalkyl, phosphonylalkyl, alkenyl, or aralkyl of $R^1$ and $R^2$ may be substituted or unsubstituted. Substitution may include solubilizing groups such as ammonium groups, phosphonium groups, pyridinium groups, or other solubility enhancing groups as described in U.S. Pat. No. 6,445,486.

In one aspect, an electrochemical device is provided, which includes a non-dimerizing electrochromic compound represented by Formula (III):

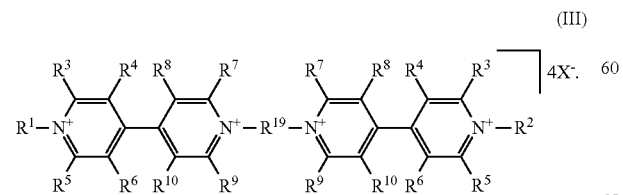
(III)

For compounds of Formula (III), $R^{19}$ is $(CH_2)_{n'}$ or arylene, and n' is from 1 to 12, and $R^1$, $R^3$-$R^{10}$ and X are as defined herein for Formula (I). In some embodiments, $R^{19}$ is $(CH_2)_{n'}$, wherein n' is from 1-10. In some embodiments, $R^{19}$ is $(CH_2)_{3-8}$. In other embodiments, $R^{19}$ is phenylene. In some embodiments, $R^{19}$ is 1,4-phenylene.

In one aspect, an electrochemical device is provided, which includes a non-dimerizing electrochromic compound represented by Formula (IV):

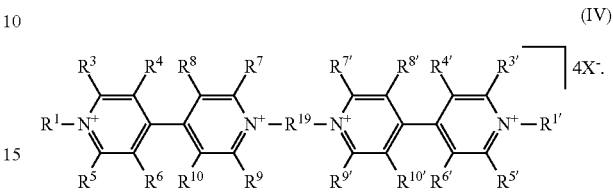
(IV)

For compounds of Formula (IV), $R^1$ and $R^{1'}$ may be individually alkyl, siloxyalkyl, hydroxyalkyl, alkylcarboxylate, alkylphosphonate, alkylisocyanate, alkenyl, or aralkyl; $R^4$, $R^6$, $R^8$, $R^{10}$, $R^{4'}$, $R^{6'}$, $R^{8'}$, and $R^{10'}$ may be individually H, $OR^{20}$, F, Cl, Br, I, CN, $NO_2$, alkyl, or aryl; and $R^3$, $R^5$, $R^7$, $R^9$, $R^{3'}$, $R^{5'}$, $R^{7'}$, and $R^{9'}$ may be individually H, $OR^{20}$, F, Cl, Br, I, CN, $NO_2$, alkyl, or aryl, with the proviso that $R^3$, $R^5$, $R^{3'}$, and $R^{5'}$ are individually secondary alkyl, tertiary alkyl, or aryl; $R^{19}$ is $(CH_2)_{n'}$ or arylene, and n' is from 1 to 12, and $R^{20}$ is H or alkyl. X is an anion as defined above.

The compound of Formula (IV) includes where $R^1$ and $R^{1'}$ may be individually alkyl, siloxyalkyl, hydroxyalkyl, alkylcarboxylate, alkylphosphonate, alkylisocyanate, carboxylate, phosphonate, isocyanate, alkenyl, or aralkyl; $R^4$, $R^{4'}$, $R^{6'}$, $R^{8'}$ and $R^{10'}$ may be individually H, OH, F, Cl, Br, I, CN, $NO_2$, alkyl, or aryl; and $R^3$, $R^5$, $R^7$, $R^9$, $R^{3'}$, $R^{5'}$, $R^{7'}$, and $R^{9'}$ may be individually H, OH, F, Cl, Br, I, CN, $NO_2$, alkyl, or aryl, with the proviso that $R^7$, $R^9$, $R^{7'}$, and $R^{9'}$ are individually secondary alkyl, tertiary alkyl, or aryl; $R^{19}$ is $(CH_2)_{n'}$ or arylene, and n' is from 1 to 12. X is an anion as defined above.

In another aspect, an electrochemical device is provided, which includes a non-dimerizing electrochromic compound represented by Formula (V)

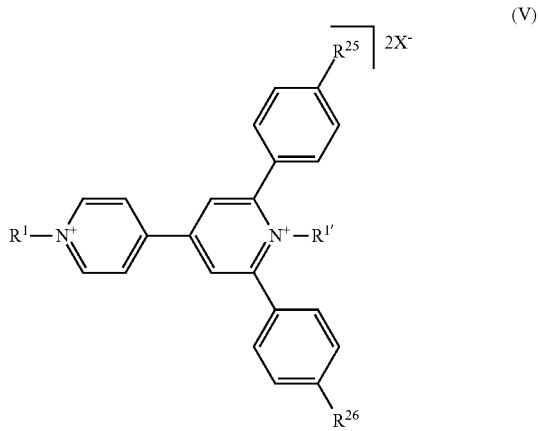
(V)

In Formula (V), $R^1$ and $R^{1'}$ are individually —$(CH_2)_n$OH, —$(CH_2)_n$Br, —$(CH_2)_n$Cl, —$(CH_2)_n$Si(OH)$_3$, —$(CH_2)_n$Si(OMe)$_3$, —$(CH_2)_n$Si(OEt)$_3$,

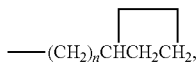

—(CH$_2$)$_n$CH=CH$_2$, —(CH$_2$)$_n$COC(O)CH=CH$_2$, or —(CH$_2$)$_n$COC(O)C(CH$_3$)=CH$_2$; R$^{25}$ and R$^{26}$ are individually H, Me, Et, Pr, OMe, OEt, OPr, OC(O)(CH$_2$)$_n$Si(OH)$_3$, OC(O)(CH$_2$)$_n$Si(OMe)$_3$, OC(O)NH(CH$_2$)$_n$Si(OEt)$_3$, OC(O)NH(CH$_2$)$_n$COOH, OC(O)NH(CH$_2$)$_n$P(O)(OH)$_2$, or OC(O)NH(CH$_2$)$_n$NCO; and n is 1 to 12.

In addition to the non-dimerizing electrochromic compound, the electrochromic medium may include at least one solvent and at least one anodic material. The non-dimerizing electrochromic compound may function as a cathodic material. The cathodic material may further comprise a polymer film, such as various substituted polythiophenes, polymeric viologens, an inorganic film, or a solid transition metal oxide, including, but not limited to, tungsten oxide.

Typically, both of the anodic and cathodic materials are electroactive and at least one of them is electrochromic. It will be understood that regardless of its ordinary meaning, the term "electroactive" will be defined herein as a material that undergoes a modification in its oxidation state upon exposure to a particular electrical potential difference. Additionally, it will be understood that the term "electrochromic" will be defined herein, regardless of its ordinary meaning, as a material that exhibits a change in its extinction coefficient at one or more wavelengths upon exposure to a particular electrical potential difference.

It is also noted, that in systems that contain a dimerizing viologen, the highly colored radical state changes at low temperature (i.e. the dimerization color is temperature dependent) is due to intermolecular interactions. There is a growth of new absorption peaks in the visible light absorption spectrum due to pairing of adjacent viologen molecules. In contrast, the color of a non-dimerizing viologen is substantially temperature independent. In other words, the color of a non-dimerizing viologen, upon reduction, is substantially consistent over a temperature range. For example, the visible light absorption spectrum of a non-dimerizing viologen radical is roughly unchanged over a temperature range of 50° C. or greater. As an illustration, the visible light absorption spectrum of a non-dimerizing viologen radical is roughly unchanged when measured at 25° C. than at –40° C.

In one aspect, an electrochromic device is provided, which includes a electrochromic medium including a non-dimerizing viologen, an anodic material, and a solvent or gel, wherein the non-dimerizing viologen exhibits an ultraviolet visible spectrum having a $\lambda_{max}$ of about 420 nm to about 680 nm. In some embodiments, the non-dimerizing viologen exhibits a $\lambda_{max}$ of greater than about 580 nm. In some embodiments, the non-dimerizing viologen exhibits a $\lambda_{max}$ of greater than about 600 nm. In some embodiments, the non-dimerizing viologen exhibits a $\lambda_{max}$ of greater than about 620 nm. In some embodiments, the non-dimerizing viologen exhibits a $\lambda_{max}$ of about 640 nm.

The electrochromic medium may include a non-dimerizing viologen as described herein. In some embodiments, the viologen includes a non-dimerizing electrochromic compound of Formula (I) wherein R$^1$ and R$^2$ may be individually alkyl, siloxyalkyl, hydroxyalkyl, alkenyl, or aralkyl; R$^3$, R$^5$, R$^7$, and R$^9$ may individually be H, OH, F, Cl, Br, I, CN, NO$_2$, alkyl, or aryl R$^4$, R$^6$, R$^8$, and R$^{10}$ may be individually H, OH, F, Cl, Br, I, CN, NO$_2$, alkyl, or aryl; and X is an anion; with the proviso that at least, R$^3$ and R$^5$ or R$^7$ and R$^9$, are individually secondary alkyl, tertiary alkyl, or aryl; and when R$^1$ and R$^2$ are each methyl, R$^3$ and R$^5$, or R$^7$ and R$^9$ are not phenyl or phenyl substituted with methyl. In other embodiments, the viologen includes a compound of Formula (III) as described herein. In some embodiments, the viologen includes a compound of Formula (IV) as described herein. In some embodiments, the viologen includes a compound of Formula (V) as described herein.

In addition to the non-dimerizing electrochromic viologen, the electrochromic medium may include at least one solvent and at least one anodic material. The non-dimerizing electrochromic viologen may function as a cathodic material. The cathodic material may further comprise a polymer film, such as various substituted polythiophenes, polymeric viologens, an inorganic film, or a solid transition metal oxide, including, but not limited to, tungsten oxide.

Typically both the anodic and cathodic materials are electroactive and at least one of them is electrochromic. It will be understood that regardless of its ordinary meaning, the term "electroactive" will be defined herein as a material that undergoes a modification in its oxidation state upon exposure to a particular electrical potential difference. Additionally, it will be understood that the term "electrochromic" will be defined herein, regardless of its ordinary meaning, as a material that exhibits a change in its extinction coefficient at one or more wavelengths upon exposure to a particular electrical potential difference.

Illustrative anodic materials include oxidizable species. Illustrative anodic materials may include, but are not limited to, metallocenes, 5,10-dihydrophenazines, phenothiazines, phenoxazines, carbazoles, triphenodithiazines, triphendioxazines, and related compounds. Anodic materials included in the electrochromic medium may include any one of a number of materials including ferrocene, substituted ferrocenes, substituted ferrocenyl salts, phenazine, substituted phenazines, phenothiazine, substituted phenothiazines, including substituted dithiazines, thianthrene, and substituted thianthrenes. Examples of anodic materials may include di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), and 3,10-dimethoxy-7,14-(triethylammoniumbutyl)-triphenodithazinebis (tetrafluoroborate).

It is also contemplated that the anodic material may include a polymer film, such as polyaniline, polythiophenes, polymeric metallocenes, or a solid transition metal oxide, including, but not limited to, oxides of vanadium, nickel, iridium, as well as numerous heterocyclic compounds, etc. It will be understood that numerous other anodic materials are contemplated for use including those disclosed in U.S. Pat. Nos. 4,902,108; 6,188,505; 6,710,906; and 7,428,091. In another embodiment, at least one of the anodic electroactive material includes a substituted or unsubstituted phenazine compound. In another embodiment, at least one of the anodic electroactive material includes a substituted or unsubstituted 2,7-dialkyl-5,10-dialkyl-5,10-dihydrophenazine compound. In another embodiment, at least one alkyl group of the 5,10-dialkyl groups attached to the phenazine compound includes at least 4 carbon atoms and is void of any β hydrogen atoms, and at least one alkyl group of the 2,7-dialkyl groups attached to the phenazine compound includes at least 4 carbons. In another embodiment, at least one alkyl group of the 5,10-dialkyl groups attached to the phenazine compound includes a substituted or unsubstituted neopentyl group, and at least one alkyl group of the 2,7-dialkyl groups attached to the phenazine compound includes a substituted or unsubstituted isopropyl, isobutyl, (2-ethylbutyl), or (2-propylpentyl) group. In some embodiments, at least one alkyl group of the 5,10-dialkyl groups attached to the phenazine compound includes a neopentyl group, and at least one alkyl group of the 2,7-dialkyl groups attached to the phenazine compound includes a 2-ethyl-1-butanol group. In another embodiment, at least one alkyl group of the 5,10-dialkyl groups attached to the phenazine compound includes a neopentyl group, and at least one alkyl group of the 2,7-dialkyl groups attached to the phenazine compound includes an isobutyl group.

In some embodiments, a solvent of the electrochromic medium may include, but is not limited to, 3-methylsulfolane, dimethyl sulfoxide, dimethyl formamide, tetraglyme and other polyethers; alcohols such as ethoxyethanol; nitriles, such as acetonitrile, glutaronitrile, 3-hydroxypropionitrile, and 2-methylglutaronitrile; ketones including 2-acetylbutyrolactone, and cyclopentanone; cyclic esters including beta-propiolactone, γ-butyrolactone, γ-valerolactone; propylene carbonate (PC), ethylene carbonate; oligoethers; ionic liquids, such as pyridinium-, imidazolium-, and pyrrolidinium-compounds; and homogenous mixtures of any two or more such solvents. Where the solvent includes an ionic liquid, the counterion may be $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $N(CF_3SO_2)_2^-$, $C(CF_3SO_2)_3^-$, $N(SO_2C_2F_5)^-$, $^-Al(OC(CF_3)_3)_4$ or $^-BAr_4$ where Ar is a aryl or fluorinated aryl group, or other counterions used in ionic liquids. In one embodiment, the counterion is $^-BAr_4$ and Ar is a pentafluorophenyl group. In another embodiment, the electrochromic composition may include a solvent that includes propylene carbonate. While specific solvents have been disclosed as being associated with the electrochromic composition, numerous other solvents that would be known to those having ordinary skill in the art having the present disclosure before them are likewise contemplated for use. For example, in addition to the solvent, the electrochromic medium may be a gel composition.

In the electrochromic medium, one or more materials may undergo a change in phase during the operation of the device, for example a material contained in solution in the ionically conducting electrolyte forms a layer on the electrically conducting electrode when electrochemically oxidized or reduced.

In addition, the electrochromic medium may include other materials, such as light absorbers, light stabilizers, thermal stabilizers, antioxidants, oxygen scavengers, thickeners, viscosity modifiers, tint providing agents, redox buffers, and mixtures of any two or more such materials. Illustrative UV-stabilizers may include, but are not limited to, 2-ethyl-2-cyano-3,3-diphenyl acrylate; (2-ethylhexyl)-2-cyano-3,3-diphenyl acrylate; 2-(2'-hydroxy-4'-methylphenyl)benzotriazole, sold by Ciba-Geigy Corp. under the trademark Tinuvin P; 3-[3-(2H-benzotriazole-2-yl)-5-(1,1-dimethylethyl)-4-hydroxyphenyl]propionic acid pentyl ester prepared from Tinuvin 213, sold by Ciba-Geigy Corp., via conventional hydrolysis followed by conventional esterification (hereinafter "Tinuvin PE"); 2,4-dihydroxybenzophenone; 2-hydroxy-4-methoxybenzophenone; and 2-ethyl-2'-ethoxyalanilide.

In one embodiment, the electrochromic medium further includes an anodic and/or cathodic color-stabilizing redox buffer. Suitable redox buffers include, among others, those disclosed in U.S. Pat. No. 6,188,505. Other examples of suitable anodic and cathodic redox buffers include, but are not limited to, metallocene (e.g., substituted ferrocenes), and metallocinium (e.g. ferrocinium) compounds.

In one embodiment, the electrochromic medium may further include a cross-linked polymer matrix, a free-standing gel, and/or a substantially non-weeping gel.

The electrochromic medium may be made up in layers and includes a material attached directly to an electrically conducting electrode or confined in close proximity thereto which remains attached or confined when electrochemically oxidized or reduced.

In one aspect, an electrochromic device is provided which includes an electrochromic medium comprising the non-dimerizing electrochromic compound as described herein and at least one chamber defined by a first conductive surface of first substrate, a second conductive surface of a second substrate, and a sealing member joining the first substrate to the second substrate. The electrochromic medium is disposed within the chamber. The first and second substrates may be off-set to one another to allow for electric contact to be made with the first and second conductive surfaces.

A schematic representation of an electrochromic device is shown in FIG. 1. The electrochromic device 100 includes first substrate 112 having a front surface 112A and a rear surface 112B, and a second substrate 114 having a front surface 114A and a rear surface 114B. The front surface 112A and the front surface 114A have associated therewith conductive surfaces 118 and 120, respectively. The first substrate 112 and the second substrate 114, along with a sealing member 122 define a chamber 116 for containing an electrochromic medium 124. The device also includes one or more plugs 126 and 130 associated with one or more fill ports 128. The one or more fill ports 128 may be disposed within the first substrate 112, the second substrate 114, or the sealing member 122. Upon mounting as a mirror, window, or other device, the electrochromic device 100 may optionally include a bezel that extends around a periphery of at least one of the first substrate 112 and the second substrate 114 to conceal and/or protect a bus connector (if present), the sealing member 122, one or more plugs 126 and 130, and the one or more fill ports 128.

Several other electrochromic device configurations are contemplated for use, including, but not limited to, those disclosed in U.S. Pat. Nos. 5,818,625; 6,597,489; and 6,700,692, all of which are hereby incorporated herein by reference in their entirety including all references incorporated therein.

In some embodiments, the first substrate may be fabricated from any one of a number of materials that are transparent or substantially transparent in the visible region of the electromagnetic spectrum, such as, for example, borosilicate glass, soda lime glass, natural and synthetic polymeric resins, plastics, and/or composites including polyesters (e.g. PET), polyimides (PI), polycarbonates, polysulfones, polyethylene naphthalate (PEN), ethylene vinyl acetate (EVA), acrylate polymers, as well as Topas®. In another embodiment, the first substrate is fabricated from a sheet of glass having a thickness ranging from about 0.10 millimeters (mm) to about 12.7 mm. This may include any range of thickness such as from about 0.50 mm to about 1.50 mm, or from about 0.65 mm to about 1.00 mm. Of course, the thickness of the substrate will depend upon the particular application of the electrochromic device. While particular substrate materials have been disclosed, for illustrative purposes only, it will be understood that numerous other substrate materials are likewise contemplated for use—so long as the materials are at least substantially transparent and exhibit appropriate physical properties, such as strength, to be able to operate effectively in conditions of intended use.

Indeed, electrochromic devices in accordance with the present invention can be, during normal operation, exposed to extreme temperature variation as well as substantial UV radiation, emanating primarily from the sun. It will be further understood that first substrate and/or second substrate may comprise a UV absorbing layer and/or contain a UV absorbing material to help protect the substrate(s) and/or the electrochromic media from UV damage.

In some embodiments, the second substrate may be fabricated from similar materials as that of the first substrate, or where transparency of the second substrate is not desired, the second substrate may be a metal. The second substrate is fabricated from a sheet of glass or plastic having a thickness ranging from about 0.10 mm to about 12.7 mm. This may include thicknesses from about 0.50 mm to about 1.50 mm, or from about 0.65 mm to about 1.00 mm. If the first and second substrates are fabricated from sheets of glass, then the glass can optionally be tempered, heat strengthened, chemically strengthened, and/or laminated prior to or subsequent to being coated with layers of electrically conductive material.

One or more layers of electrically conductive material may be associated with the rear surface of the first substrate. These layers serve as an electrode for the electrochromic device. Electrically conductive material is desirably a material that: (a) is substantially transparent in the visible region of the electromagnetic spectrum; (b) bonds reasonably well to the first substrate; (c) maintains this bond when associated with a sealing member; (d) is generally resistant to corrosion from materials contained within the electrochromic device or the atmosphere; and (e) exhibits minimal diffuse or specular reflectance as well as sufficient electrical conductance. It is contemplated that the electrically conductive material may be fabricated from fluorine doped tin oxide (FTO), for example TEC glass, indium/tin oxide (ITO), doped zinc oxide, indium zinc oxide, metal oxide/metal/metal oxide (wherein metal oxide can be substituted with metal carbide, metal nitride, metal sulfide, etc.), or other materials known to those having ordinary skill in the art.

One or more layers of an electrically conductive material made of the same or different materials as those associated with the rear surface of the first substrate may be associated the front surface of the second substrate. The electrically conductive material may be operatively bonded to electrically conductive material associate with the first substrate by a sealing member. Once bonded, the sealing member, plug and/or the juxtaposed portions of electrically conductive materials may serve to generally define an inner peripheral geometry of a chamber. Alternatively, edge sealing techniques may be utilized which are disclosed in U.S. Pat. No. 7,372,611.

In some embodiments, the first substantially transparent substrate and second substantially transparent substrate have a cell distance of less than 600 µm. In another embodiment, the first substantially transparent substrate and second substantially transparent substrate have a cell distance of about 150 µm to about 600 µm, about 200 µm to about 300 µm, about 225 µm to about 275 µm, or ranges between any two of these values (including endpoints). In another embodiment, the first substantially transparent substrate and second substantially transparent substrate have a cell distance of about 350 µm, 300 µm, 275 µm, 250 µm, 225 µm, 200 µm, 175 µm, 150 µm, or ranges between any two of these values (including endpoints). In another embodiment, the first substantially transparent substrate and second substantially transparent substrate have a cell distance of about 250 µm.

In some embodiments, the sealing member may include any material that is configured to adhesively bond to the electrically conductive materials coated on the first and second substrate to, in turn, seal a chamber, (in certain embodiments in cooperation with a plug and fill port so that electrochromic composition does not inadvertently leak out of the chamber. It is also contemplated that the sealing member extends all the way to rear surface and front surface of their respective substrates. In such an embodiment, the layers of electrically conductive material coated on the first and second substrates may be partially removed where the sealing member is positioned. If the electrically conductive materials are not associated with their respective substrates, then the sealing member preferably bonds well to glass. It will be understood that sealing member can be fabricated from any one of a number of materials including, for example, those disclosed in U.S. Pat. Nos. 4,297,401; 4,418,102; 4,695,490; 5,596,023; 5,596,024; 6,157,480; and 6,714,334.

In some embodiments, the concentration of the anodic and/or cathodic materials in the electrochromic medium may be from about 1 millimolar (mM) to about 500 mM. In some embodiments, the concentration of the anodic and/or cathodic materials in the electrochromic medium may be from about 2 mM to about 100 mM.

In one embodiment, at least one of the anodic electroactive materials has a concentration of at least 5 mM. In another embodiment, at least one of the anodic electroactive materials has a concentration of about 2 mM to about 100 mM, about 5 mM to about 50 mM, about 7 mM to about 50 mM, or ranges between any two of these values (including endpoints). In another embodiment, at least one of the anodic electroactive materials has a concentration of about 5 mM to about 7 mM. In another embodiment, a second anodic electroactive material has a concentration of about 40 mM to about 50 mM.

In one embodiment, at least one of the cathodic electroactive materials has a concentration of at least 50 mM. In another embodiment, at least one of the cathodic electroactive materials has a concentration of about 50 mM to about 100 mM, about 60 to about 90 mM, about 70 mM to about 80 mM, or ranges between any two of these values (including endpoints).

Illustrative electrochromic devices employing the electrochromic compounds described herein may include, for illustrative purposes only, a window, an aircraft transparency, a mirror, a display device, and the like. It will be understood that like or analogous elements and/or components, and/or methods referred to herein, may be identified throughout the drawings with like reference characters. In some embodiments, the electrochromic device is an electrochromic window or an electrochromic mirror. In some embodiments, the device is a vehicular interior electrochromic mirror. In some embodiments, the device is a variable transmission electrochromic window. In some embodiments, the device is an aircraft window system. Other applications of the electrochromic device includes screens for watches, calculators and computer display screens; eye wear such as eyeglasses and sunglasses; switchable mirrors, sun visors; automobile, architectural, aircraft, marine, and spacecraft windows; information display boards and digital billboards and the like.

The electrochromic devices described herein have superior properties since they avoid precipitation of the viologen caused by dimerization thereof and the resulting deterioration of the electrochromic device.

The present invention, thus generally described, will be understood more readily by reference to the following examples, which are provided by way of illustration and are not intended to be limiting of the present invention.

EXAMPLES

The following examples more specifically illustrate protocols for preparing compounds and devices according to various embodiments described above. These examples should in no way be construed as limiting the scope of the present technology.

Example 1: Cathodic Compounds: A Non-Dimerizing Viologen

A non-dimerizing viologen diol was prepared through a 4-step reaction:

Step 1:
1,5-Di-p-tolyl-3-(4-pyridyl)pentane-1,5-dione

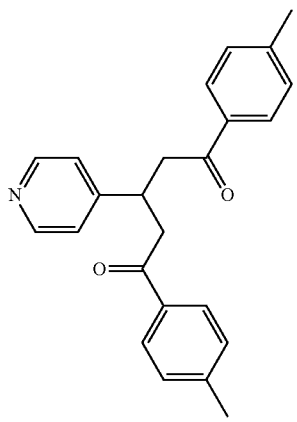 [SMILES: Cc1ccc(C(=O)CC(CC(=O)c2ccc(C)cc2)c2ccncc2)cc1]

Pyridine-4-carboxaldehyde (17 g, 0.14 moles) and 4-methylacetophenone (80 g, 0.6 moles) in 150 ml of ethanol were mixed with a solution of KOH (6%) in ethanol-water (2:1, 150 ml). The mixture was refluxed for 45 min under $N_2$ with stirring and then cooled to room temperature. The solution was concentrated under reduced pressure until crystals began to separate. The crude product was recrystallized from hot ethanol to produce white needles. Yield: 26 g, 48%

Step 2: 1,5-Di-p-tolyl-3-(1-(11-hydroxyundecyl)-4-pyridinium)pentane-1,5-dione bromide

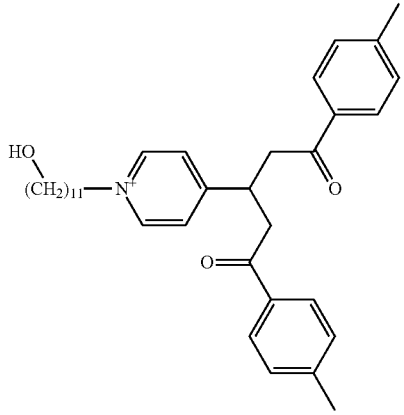

A solution of 11-bromoundecan-1-ol (15 g, 0.06 mole) and 1,5-di-p-tolyl-3-(4-pyridyl)pentane-1,5-dione (15 g, 0.04 mole) in 100 ml of acetonitrile was refluxed for overnight. On cooling, an off-white solid precipitated out. The solid was collected by filtration, washed with acetone then ether, and dried in air. Yield: 25 g, 98%. The bromide salt was changed to the tetrafluoroborate salt by metathesis using sodium tetrafluoroborate in hot water solution.

Step 3: 2,6-Di-p-tolyl-4-(1-(11-hydroxyundecyl)-4-pyridinium)pyrylium bis(tetrafluoroborate)

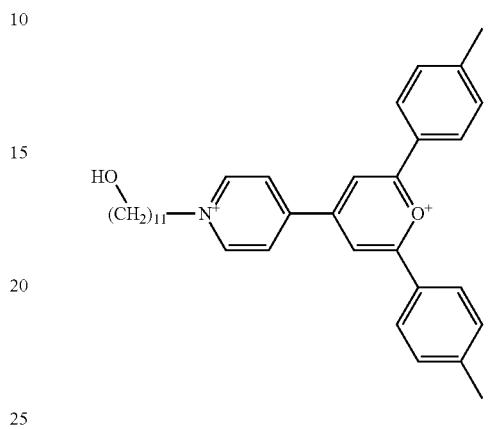

A solution of 1,5-di-p-tolyl-4-(1-(11-hydroxyundecyl)-4-pyridinium)pentane-1,5-dione tetrafluoroborate (3.1 g 5 mole) in 20 ml of acetic anhydride was slowly added to a solution of triphenymethanol (1.3 g, 5 mole) and $HBF_4$.ether (50-55% in ether, 1.4 ml, 5.1 mole) in 30 ml of acetic anhydride at 0° C. The solution was stirred for 30 min then heated to reflux for overnight. The reaction mixture was allowed to cool to room temperature then further cooled in a refrigerator. The dark red solid was collected by filtration and washed with ethyl ether. Yield: 2.7 g, 77%.

Step 4: 1'-(11-hydroxyundecyl)-1-(5-hydroxypentyl)-2,6-di-p-tolyl-4,4'-bipyridinium Bis(bis(trifluoromethane)sulfonimide) ("1'-(11-hydroxyundecyl)-1-(5-hydroxypentyl)-2,6-di-p-tolyl-viologen Bis (TFSI)")

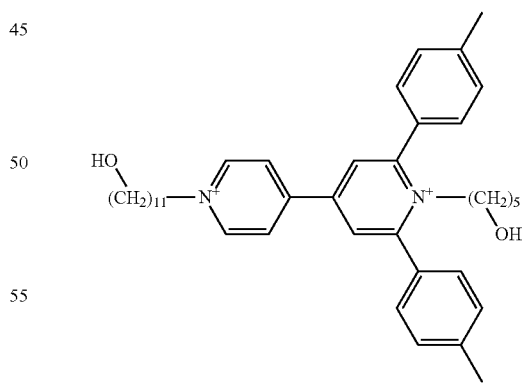

A solution of 5-aminopentan-1-ol (11 g, 0.10 mol) in 20 ml of acetic acid was added to the solution of 2,6-di-p-tolyl-4-[1-(11-hydroxyundecyl)-4-pyridinium]pyrylium bis(tetrafluoroborate) in 100 ml of acetic acid. The mixture was heated to 50° C. under $N_2$ with stirring for 3 hours. After cooling, the solvent was removed by rotary evaporation. The residue was washed with diethyl ether and dried in air. The hydroxyl groups of the crude product are partially esterified by acetic acid. To hydrolyze the ester groups, the crude product was dissolved in 100 ml methanol and 100 ml 1M HCl. The mixture was heated to reflux for 30 min. The volatile solvents in the mixture were partially removed by distillation until the IR spectrum of the residue no longer showed an ester peak at 1740 cm$^{-1}$. 40 g of lithium TFSI was added to the mixture causing the desired product to separate. The oil was extracted with 4-methyl-2-pentanone, dried with MgSO$_4$, and the solvent was removed by rotary evaporation. A pale-brown oil was collected. Yield: 23 g, 92%.

Example 2. Viologen Diol

For comparison, a viologen diol was prepared using the following procedure.

1,1'-di(11-hydroxyundecyl)-viologen bis(TFSI)

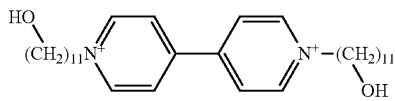

A mixture of 4,4'-bipyridine (25 g) and 11-bromoundecan-1-ol (100 g) in 800 ml of acetonitrile was refluxed for 24 hours under N$_2$ atmosphere yielding a precipitate. After cooling to room temperature, the solid was collected by filtration, washed with acetone, and then dried in a vacuum oven. The bromide salt was converted to the TFSI salt by metathesis with lithium TFSI in water. The resulting oil was extracted from the aqueous solution with 4-methyl-2-pentanone and dried with MgSO$_4$. The solvent was removed by rotary evaporation under reduced pressure to provide 1,1'-di(11-hydroxyundecyl)-4,4'-bipyridinium bis(TFSI). Yield: 75%.

Example 3. Analytical Methods

Figure 2:
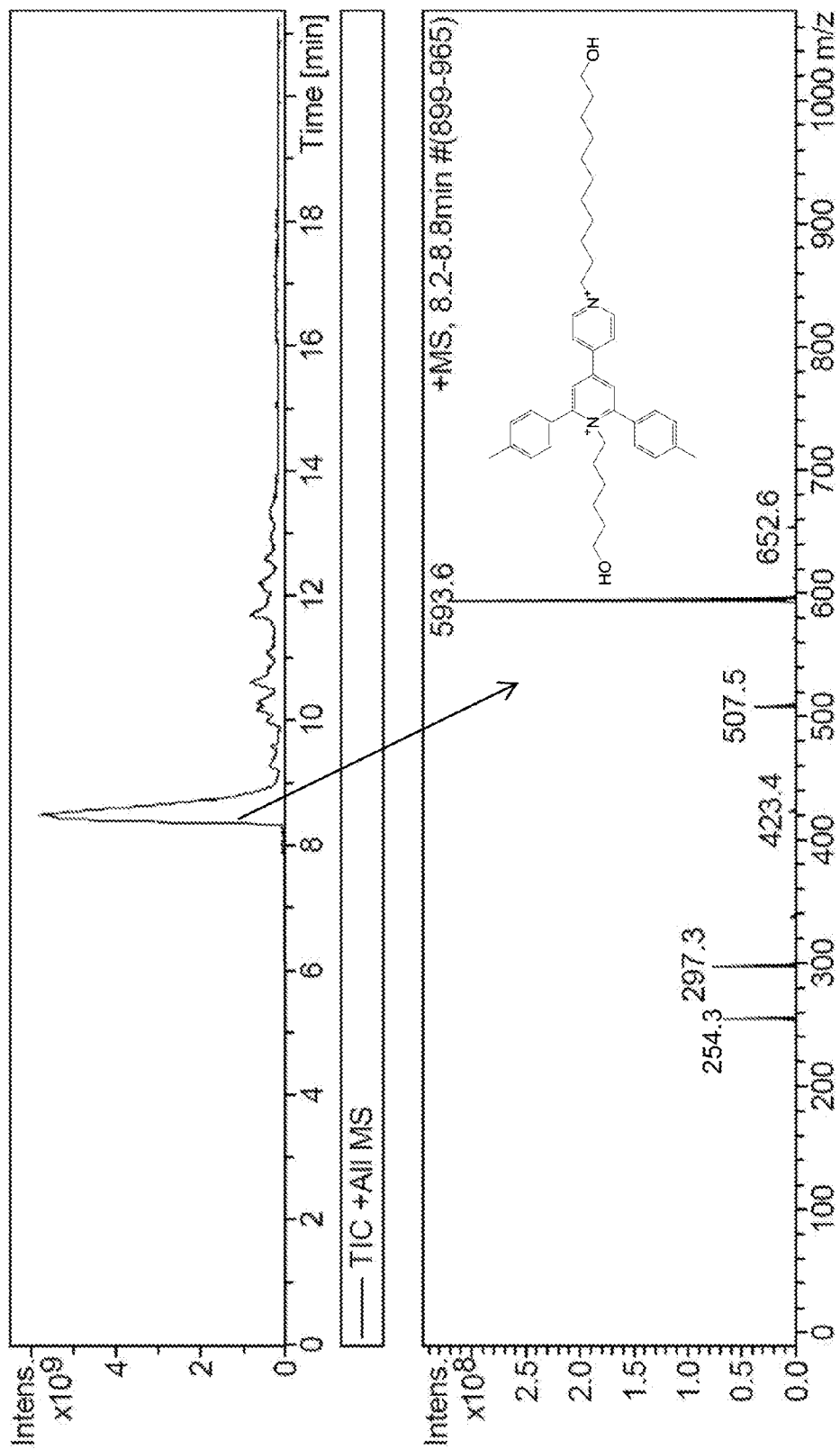
FIG. 2 is a HPLC chromatograph of a sample of 1'-(11-hydroxyundecyl)-1-(5-hydroxypentyl)-2,6-di-p-tolyl-4,4'-bipyridinium bis(bis(trifluoromethane)sulfonamide), according to the examples.

HPLC/MS: Reactions were monitored by high pressure liquid chromatography/MS equipped with a YMC-PACK, C4 column (4.6 mm×50 mm×3.5 µm) connected to a UV-visible detector and monitored at a wavelength of 254 nm. A chromatogram of 1'-(11-hydroxyundecyl)-1-(5-hydroxypentyl)-2,6-di-p-tolyl-viologen bisTFSI is depicted in FIG. 2.

Figure 3:
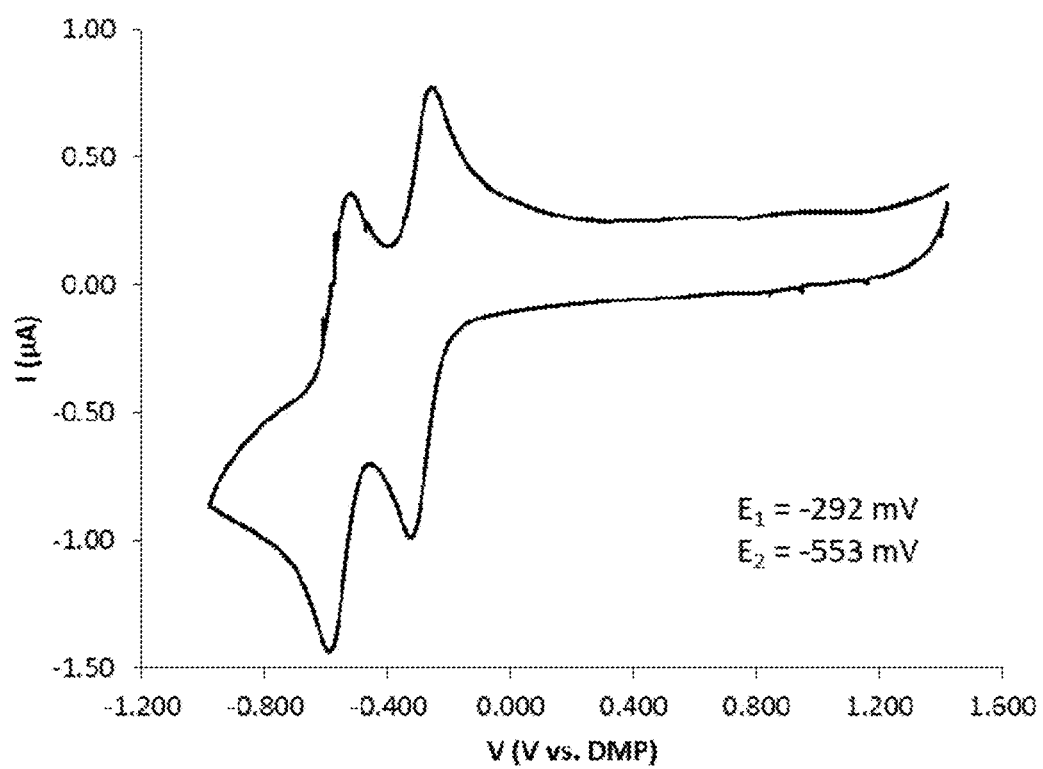
FIG. 3 is a cyclic voltammogram (CV) for a cell containing a 1 mM solution of 1'-(11-hydroxyundecyl)-1-(5-hydroxypentyl)-2,6-di-p-tolyl-4,4'-bipyridinium bis(bis(trifluoromethane)sulfonimide) and 0.2M TEABF$_4$ (tetraethylammonium tetrafluoroborate) in degassed propylene carbonate (PC) at room temperature with a Pt working electrode and 50 mV/s potential scan rate, according to the examples.

Cyclic voltammetry (CV). Cyclic voltammogram used a Pt button working electrode, Pt wire counter electrode, and Ag wire pseudo-reference electrode. Samples consisted of 1 millimolar solution of sample, in this case 1'-(11-hydroxyundecyl)-1-(5-hydroxypentyl)-2,6-di-p-tolyl-4,4'-bipyridinium bis(TFSI), dissolved in an electrolyte of 0.2M tetraethylammonium tetrafluoroborate (TEABF$_4$) in degassed propylene carbonate. Results are shown in FIG. 3. The voltammogram was recorded at room temperature at 50 mV/s scan rate and showed two reversible waves at −270 mV and −550 mV versus a reference of 5,10-dimethylphenazine in which the first oxidation is set to 300 mV.

Example 4. A Ferrocene Diol

Ferrocene diol was prepared through a 4-step reaction:

Step a: Preparation of 1,1'-di(6-bromohexanoyl)ferrocene

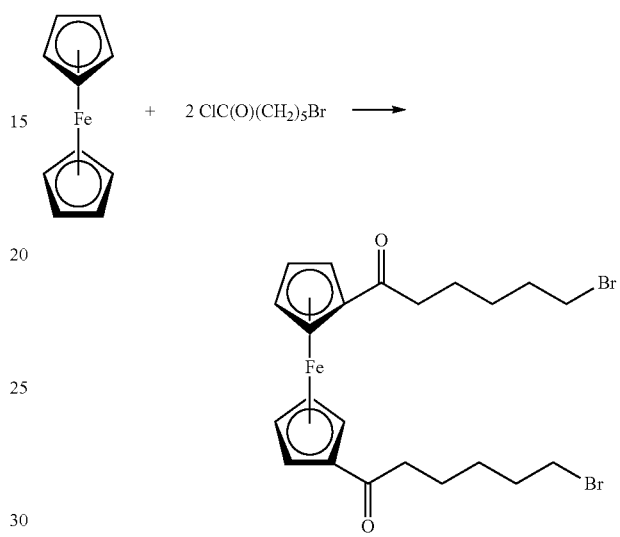

The reaction was conducted in a three-necked round-bottomed flask that was equipped with an overhead stirrer, addition funnel, and nitrogen inlet at room temperature. AlCl$_3$ (72 g, 0.54 mole) and 6-bromohexanoyl chloride (116 g, 0.54 mole) were dissolved in 250 ml of dry dichloroethane. The solution was stirred for 15 min, then placed in an addition funnel and slowly added to a solution of ferrocene (50 g, 0.27 mole) in 400 ml of dry dichloroethane at room temperature yielding a purple solution. The solution was stirred overnight. The mixture was slowly poured over ice to form two layers. The layers were separated and the organic layer (dichloroethane) was washed with 150 ml water three times. The dichloroethane solution was dried with MgSO$_4$ the dichloroethane was removed by rotary evaporation. The residue was dried under vacuum overnight. Yield: ~98%.

Step b: Preparation of 1,1'-di(6-bromohexyl)ferrocene

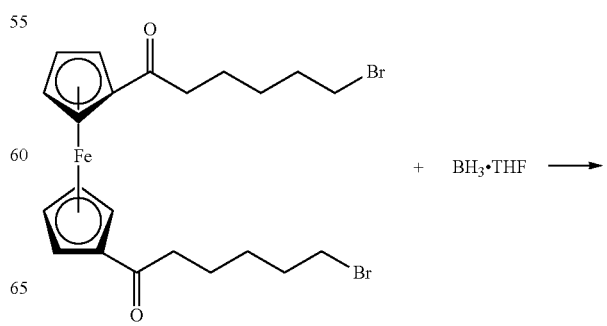

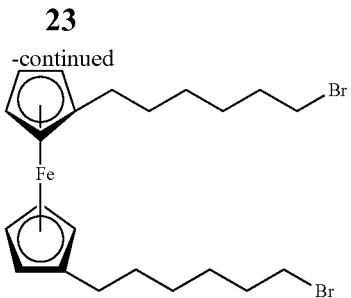

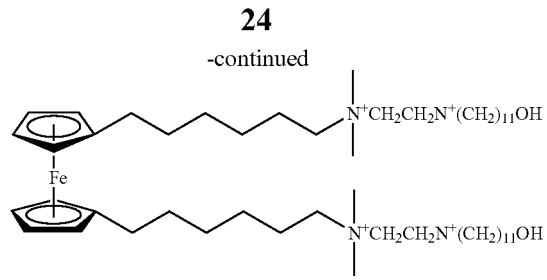

The reaction was conducted in a three-necked round-bottomed flask (500 mL) that was equipped with an overhead stirrer, addition funnel, condenser and nitrogen inlet. Borane tetrahydrofuran complex solution (1M in THF, 100 mL) was slowly added through an additional funnel to a stirred solution of 1,1'-di(6-bromohexanoyl)ferrocene (20.8 g, 38.5 mmol) in 100 ml of THF at 0° C. The reaction temperature was slowly allowed to rise to room temperature and allowed to continue overnight. The reaction mixture was heated at 70° C. for 3-4 hours followed by cooling back to room temperature. The reaction mixture was carefully quenched with ethanol and the solvents were removed by rotary evaporation. The residue was dissolved in 150 ml of diethyl ether. The solution was washed with 75 ml of HCl aqueous solution (1M) and neutralized with $NaHCO_3$ solution (1M). Finally, the diethyl ether solution was washed with DI water (100 ml) until the pH of solution was about 7. The diethyl ether solution was dried over $MgSO_4$ then the solvent was removed by rotary evaporation. Yield: ~95%.

Step c: [2-(dimethylamino)ethyl](11-hydroxyundecyl)dimethylammonium bromide

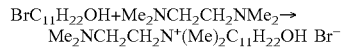

A mixture of 75 g of fresh distilled tetramethylethylenediamine and 25 g of 11-bromoundecan-1-ol in 150 ml of acetone was stirred at room temperature for overnight. The solid that formed during the reaction was collected by filtration and washed with acetone followed by ethyl ether. The desired product was collected as a white solid. Yield: 33 g, 94%. [2-(dimethylamino)ethyl](11-hydroxyundecyl)dimethylammonium TFSI was obtained by metathesis of the bromide salt with lithium TFSI in water. The desired product was extracted with ethyl acetate, dried with $MgSO_4$ then the solvent removed by rotary evaporation.

Step d: 1,1'-Bis{6-[N-(11-hydroxyundecyl)-N,N,N', N'-tetramethylethylenediammonium]-N'-hexyl}ferrocene tetra(TFSI)

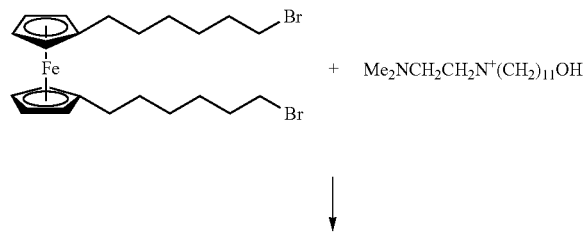

A mixture of 1,1'-di(6-bromohexyl)ferrocene (17 g, 0.033 mol) and [2-(dimethylamino)ethyl](11-hydroxyundecyl)dimethylammonium TFSI (74 g, 0.13 mol) in a mixture of MEK and acetonitrile (1:1 v/v) was refluxed overnight then was allowed to cool to room temperature yielding a yellow solid. The solid was collected by filtration then recrystallized from hot ethanol. Yield: 51% as the bromide salt. The desired product was obtained by metathesis with lithium TFSI in water.

Example 5. 1-methyl-1'-octyl-2,6-di-t-butyl viologen

Step a: Sodium 3,3-dimethyl-2-butanoate

A 100 mL round bottom flask was charged with 24 mL DMSO. The solution was cooled slightly with an ice bath but not so much to freeze the DMSO. 60 wt. % NaH in mineral oil (1.0 g, 25 mmol) was slowly added to the DMSO. After 15 minutes, 3,3-dimethyl-2-butanone (15.2 g, 152 mmol) was added slowly. Within 15 minutes the solution turned light reddish brown. The mixture was stirred for two hours.

Step b: 1,5-di-t-butyl-3-(4-pyridyl)pentane-1,5-dione

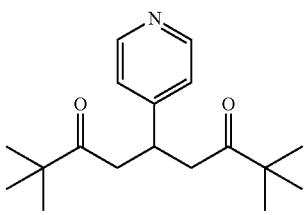 [SMILES: CC(C)(C)C(=O)CC(CC(=O)C(C)(C)C)c1ccncc1]

To the sodium 3,3-dimethyl-2-butanoate solution prepared earlier, 4-pyridine carboxaldehyde (8.0 g, 75 mmol) was slowly added. The reaction mixture was allowed to reach room temperature then stirred overnight for 16 hours during which a pale yellow solid precipitated. The solid was collected by filtration and washed with 2×80 mL $H_2O$. The solid was then suspended in 200 mL hexane for two hours, collected by filtration, resuspended in 200 mL hexane for two hours, then finally collected by filtration and dried in vacuo. Yield 14.6 g, 63%.

Step c: 1,5-di-t-butyl-3-(4-(1-octylpyridinium))pentane-1,5-dione bromide

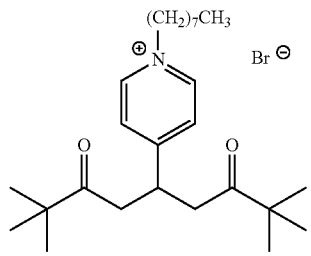

A 250 mL round bottom flask was charged with 1,5-di-t-butyl-3-(4-pyridyl)pentane-1,5-dione (14.6 g, 50 mmol), 1-octylbromide (30.0 g, 155 mmol), and 75 mL acetonitrile. The solution was stirred at room temperature for two weeks then 24 hours at reflux temperature. Upon cooling a white solid started to precipitate. The acetonitrile was removed by rotary evaporation leaving a white residue. 150 mL hexane was added to the residue to extract excess 1-octylbromide. 25 g of crude product was collected (~100% yield).

Step d: 2,6-di-t-butyl-4-(4-(1-octylpyridinium))pyrilium bis(tetrafluoroborate)

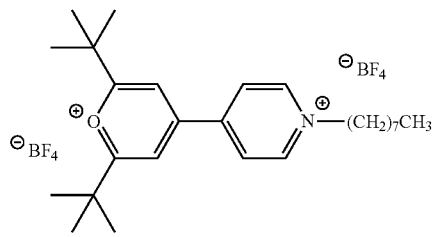

Triphenylmethanol (11.67 g, 45 mmol) was added to 55% HBF$_4$ in ether (17.0 mL) in 50 mL acetic anhydride A light yellow solid formed. This mixture was added to a 250 mL round bottom flask containing 1,5-di-t-butyl-3-(4-(1-octylpyridinium))pentane-1,5-dione bromide (9.65 g, 20 mmol) in 50 mL acetic anhydride. The mixture was heated to 50° C. for 100 minutes then cooled to RT. After 16 hours, approximately half of the solvent was removed by rotary evaporation. The solution was cooled to 0° C. during which a dark solid precipitated. The solid was collected by filtration then recrystallized twice from acetonitrile/ether to yield a light gray solid. Yield: 6.6 g, 59%

Step e: 2,6-di-t-butyl-1-methyl-1'-octyl-4,4'-bipyridinium bis(tetrafluoroborate) ("1-methyl-1'-octyl-2,6-di-t-butyl viologen")

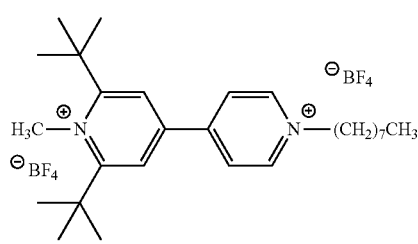

Methylamine hydrochloride (5.0 g, 74 mmol) was neutralized by addition of KOH (5.0 g, 122 mmol) in a bilayer solution of H$_2$O and CH$_2$Cl$_2$. The organic layer was separated and to it was added 2,6-di-t-butyl-4-(4-(1-octylpyridinium))pyrilium bis(tetrafluoroborate) (0.2 g, 0.36 mmol) plus 10 mL acetic acid. The solution turned purple and was heated to 50° C. for 20 hours. Upon exposure to air, the purple color dissipated. The desired product was isolated by precipitating the solution in 1:1 acetone/ether. 100% purity by LC/MS.

Example 6. Synthesis of 4,4'-[3-(triphenyl phosphonium)propyl]-1,1'-dipyridinium tetra(tetrafluoroborate) ("triphenylphosphoniumpropyl viologen" or "TPPV")

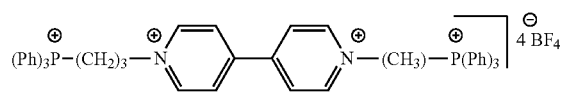

To a 2 L one-neck round bottom flask was added 1,3-dibromopropane (1 mole), triphenyl phosphine (1 mole) and acetone (1.0 L). This mixture was mildly refluxed for 1 week followed by cooling the reaction slurry to room temperature. The 1-bromo-3-(triethyl ammonium) propane bromide was then filtered and rinsed with acetone to remove impurities. An aqueous 40% tetrafluoroborate solution (500 mL) was prepared, heating to 80° C., and the bromide salt dissolved therein. The solution was then cooled to room temperature whereupon the metathesis product (the tetrafluoroborate salt) precipitated out of solution as white crystals. This tetrafluoroborate salt was filtered and washed with cold water and then dried.

In the next step, 4,4'-dipyridyl (256 mmol.) and the tetrafluoroborate salt formed above (780 mmol) were charged to a 2 L reactor with acetonitrile (800 mL). The mixture was heated to reflux for approximately 3 days until completion of the reaction. The solvent was then removed and the remaining solid dissolved in a 1:1 water:methanol mixture (1.0 L) at a temperature of 80° C., followed by addition of an aqueous 40% sodium tetrafluoroborate solution (500 mL), whereupon the mixture was cooled to room temperature and the tetrafluoroborate salt precipitated as a white solid. Filtration followed by washing with cold water provided the crude product.

The crude product was dissolved in a 80° C. 1:1 water:methanol solution (1.2 L) followed by addition of an aqueous 40% sodium tetrafluoroborate solution (100 mL). Upon cooling to room temperature a solid precipitated from solution, whereupon the solid was isolated by filtration and dried to provide 4,4'-[3(triphenyl phosphonium)propyl]-1,1'-dipyridinium tetra-(tetrafluoroborate) as a white and pure crystalline solid.

Example 7. Synthesis of Propanoldimethylammoniumbutyl Viologen

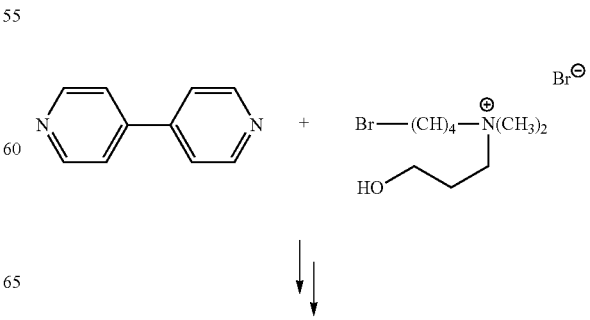

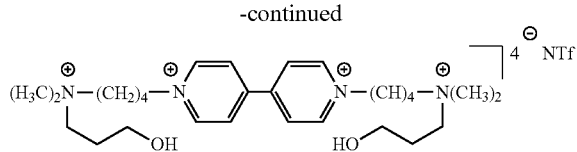

A solution of 4,4'-bipyridine (5.0 g; 32 mmol), 4-bromo-N-(3-hydroxypropyl)-N,N-dimethylbutan-1-aminium bromide (30.6 g; 92.7 mmol), and acetonitrile (100 mL) were combined and heated to reflux for 48 hours. The mixture was then cooled to room temperature and resulting solid bromide salt was collected by filtration.

The bromide salt was subsequently dissolved in water (100 mL) and heated to 50° C. Lithium TFSI (60 g; 209 mmol) was dissolved in water (120 mL; 18 MΩ-cm reverse osmosis deoionized) and slowly added to the above solution of bromide salt, whereupon the resulting mixture was maintained at 50° C. for two hours and subsequently cooled to room temperature. Upon cooling the organic product formed an oil layer, the aqueous layer was removed and the oil layer washed with water.

The procedure of the above paragraph was then repeated. The resulting product was dissolved in 4-methyl pentanone and the organic layer washed with water three times. The organic layer was then dried with $MgSO_4$, and the solvent removed to provide the desired product.

Example 8: Preparation of Films

Indium tin oxide (ITO) with a conductivity of 12 Ω/sq on soda-lime glass was used to build EC devices. Electrochromic films were deposited on the ITO surface using a Mayer rod on draw-down coater. The thickness of film was controlled by varying the Mayer rod number. Prior to coating, the ITO surface was carefully washed with 18 MΩ-cm reverse osmosis deoionized water and dried in a vacuum oven overnight.

Example 9. Preparation of Coating Fluids, Films and Devices a. Coating Fluid for Non-Dimerized Viologen Film 0.69 g of 1'-(11-hydroxyundecyl)-1-(5-hydroxypentyl)-2,6-di-p-tolyl-viologen bis(TFSI) and 0.23 g of HDT (triisocyanate, cross-linker) were dissolved in 7.0 g of propylene carbonate containing 9 wt. % polymethacrylate (PMA, $M_w$ 54,000). Prior to coating, 110 μL of a catalyst solution of 0.6 wt. % dibutyltin diacetate in propylene carbonate was added to the mixture above.

b. Coating Fluid for Normal Viologen Film 0.75 g of 1,1'-(11-hydroxyundecyl)-4,4'-bipyridinium bis(TFSI) and 0.23 g of HDT were dissolved in 7.0 g of propylene carbonate containing 9 wt. % PMA ($M_w$ 54,000). Prior to coating, 110 μL of a catalyst solution of 0.6 wt. % dibutyltin diacetate in propylene carbonate was added to the mixture above.

c. Coating Fluid for Ferrocene Film 0.78 g of 1,1'-bis{6-[N-(11-hydroxyundecyl)-N,N,N',N'-tetramethylethylenediammonium]-N'-hexyl}ferrocene tetra(TFSI) and 0.23 g of HDT were dissolved in 7.0 g of propylene carbonate containing 9 wt. % PMA 54,000). Prior to coating, 110 μL of a catalyst solution of 0.6 wt. % dibutyltin diacetate in propylene carbonate was added to the mixture above.

d. Curing Process of Films (Preformed EC Film on ITO):

The films were cured in a 60° C. oven under $N_2$ atmosphere overnight. The cured films were dry, hard and showed no deformation when the film's surface was depressed.

Example 10. Preparation of a 3-Layer EC Device

A pre-formed viologen film and a pre-formed ferrocene gel film each on a sheet of ITO were combined into an EC cell. First, the films were removed from a small area along the edge of each electrode. An epoxy containing 500 μM glass spacer beads was deposited along the edge of the viologen electrode leaving a small hole for filling with electrolyte later. The ferrocene electrode was layered on top of the epoxy which was then cured at 160° C. for one hour. An electrolyte solution consisting of 5 wt. % polymethylacrylate-co-(2-hydroxy)ethylmethacrylate (molar ratio: 10:1), MDI (diisocyanate), 5 ppm of dibutyltin diacetate as a cross-linking catalyst, and 0.2M $TEABF_4$ supporting electrolyte was prepared. The electrolyte solution was vacuum back-filled into the EC cell. The fill port was sealed with a UV-cure sealing material. The electrolyte layer was then crosslinked in a 60° C. oven under $N_2$ atmosphere overnight.

Figure 4:
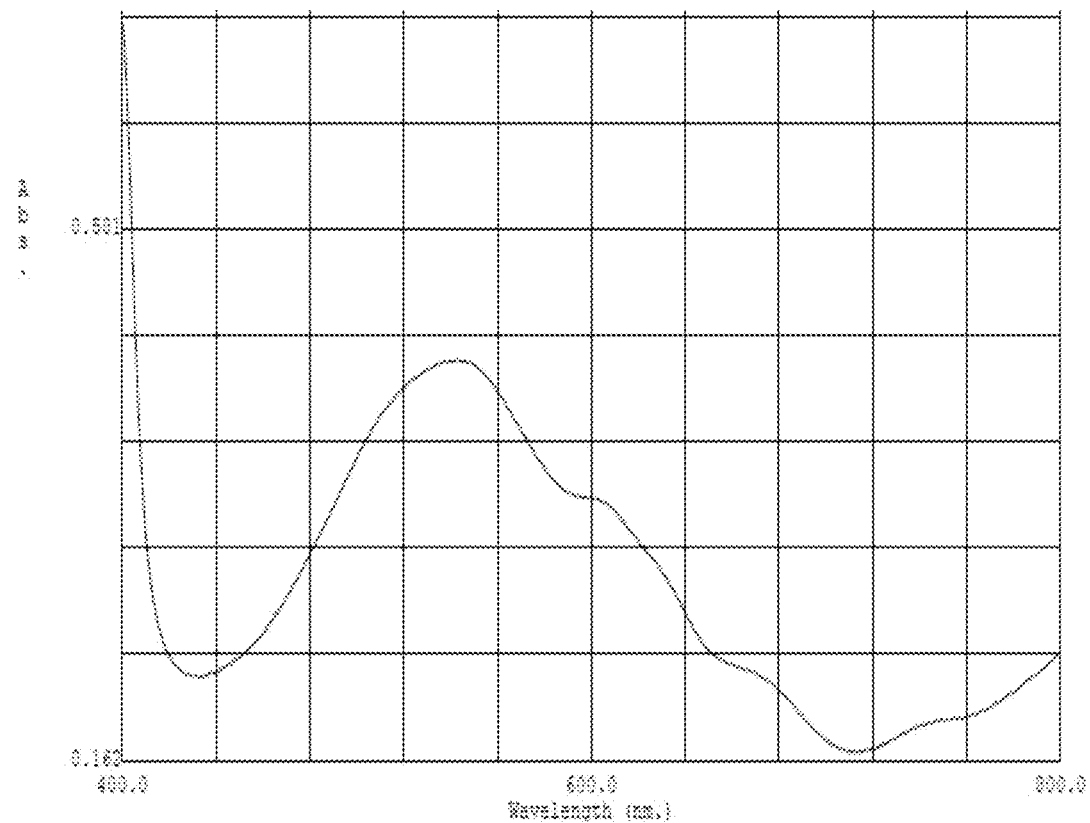
FIG. 4 is a UV-Vis absorption spectrum of a 3"×3", 3-layer electrochromic device taken in a powered state (1.2V) at room temperature, according to the examples.

Results. FIG. 4 shows the UV-Vis absorption spectrum of a 3"×3" 3-layer electrochromic device powered at 1.2V at room temperature. The device includes 1,1'-di(11-hydroxyundecyl)-4,4'-bipyridinium bis(TFSI)) polyurethane film as a cathodic layer, a 1,1'-Bis{6-[N-(11-hydroxyundecyl)-N,N,N',N'-tetramethylethylenediammonium]-N'-hexyl}ferrocene tetra(TFSI) polyurethane film as an anodic layer, and a polyacrylate gel as the electrolyte layer. The spectrum shows an absorption peak typically associated with dimerization at 540 nm.

Figure 5:
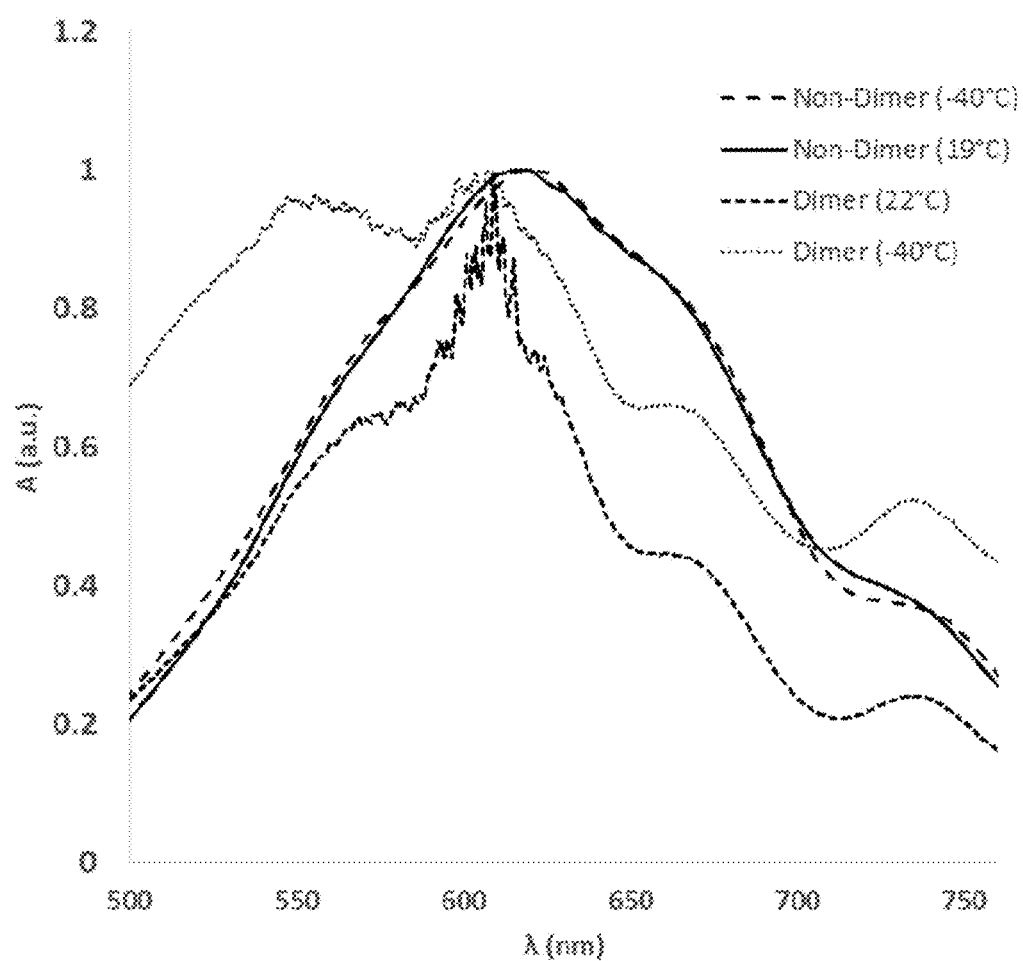
FIG. 5 is a UV-Vis absorption spectra of the radical cations of two 0.5 mM propylene carbonate solutions of the non-dimerizing viologen 1'-(11-hydroxyundecyl)-1-(5-hydroxypentyl)-2,6-di-p-tolyl-4,4'-bipyridinium bis(bis(trifluoromethane)sulfonimide) or dimerizing viologen 1,1'-dioctyl-4,4'-bipyridinium bis(tetrafluoroborate) at both 19-22° C. and −40° C., according to the examples.

FIG. 5 is a UV-Vis absorption spectra of the radical cations of two 20 mM (100 μM cell spacing) propylene carbonate solutions of non-dimerizing viologen 1'-(11-hydroxyundecyl)-1-(5-hydroxypentyl)-2,6-di-p-tolyl-viologen bis(TFSI) (referenced in FIG. 5 as "Non-Dimer") at both 22° C. and –40° C. and dimerizing viologen 1,1'-dioctyl-4,4'-bipyridinium bis(tetrafluoroborate) ("dioctylviologen") at both 19° C. and –40° C. The dioctylviologen showed a greater degree of color change with temperature especially at 550 nm. The 550 nm peak in FIG. 5 associated with dimerization and results in a greater purple coloration of the solution at lower temperatures as compared to a bluish color at room temperature.

Figure 6:
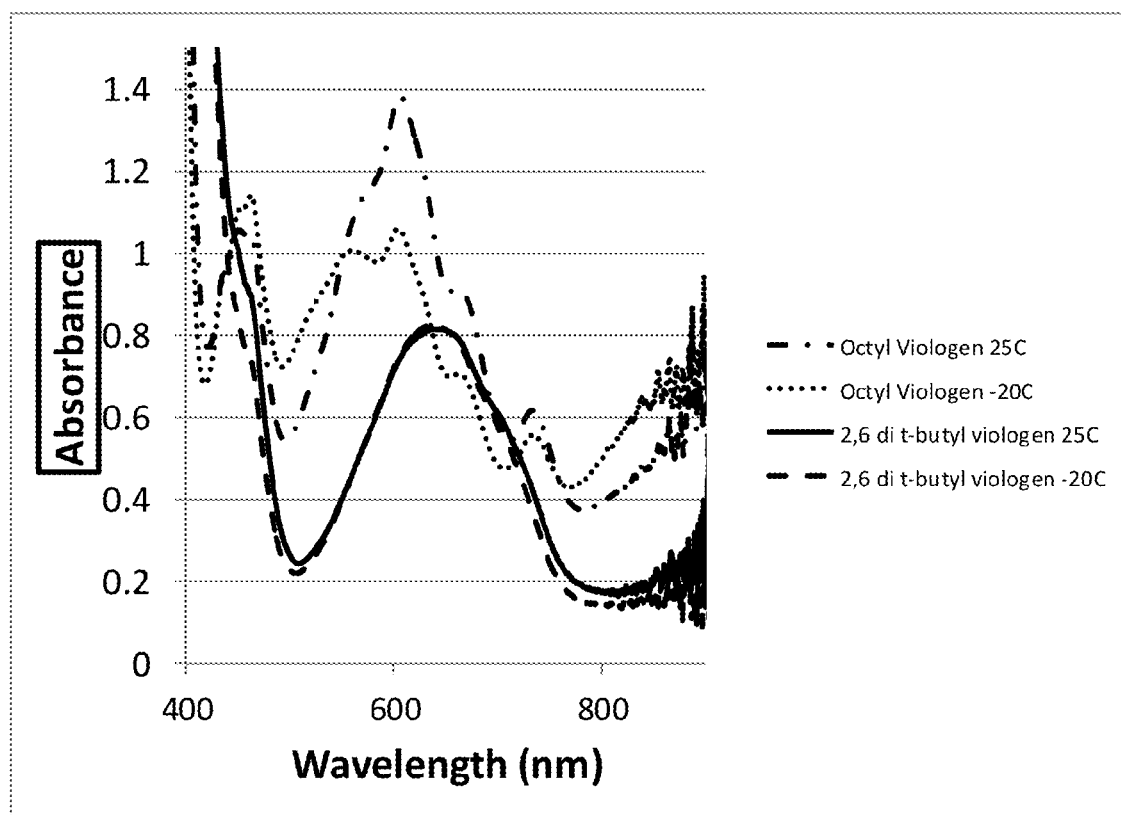
FIG. 6 is a UV-Vis absorption spectra of the radical cations of two 30 mM (90 μM cell spacing) propylene carbonate solutions of 1-methyl-1'-octyl-2,6-di-t-butyl viologen at both 22° C. and −40° C. and 1,1'-dioctyl-viologen bis(tetrafluoroborate) at both 22° C. and −40° C., according to examples.

FIG. 6 is a UV-Vis absorption spectra of the radical cations of two 30 mM (90 μM cell spacing) propylene carbonate solutions of 1-methyl-1'-octyl-2,6-di-t-butyl viologen from Example 5 at both 22° C. and –40° C. and dioctylviologen bis(tetrafluoroborate) at both 22° C. and –40° C. The dioctylviologen showed a greater degree of color change with temperature especially at 550 nm. Again, the 550 nm peak in FIG. 6 associated with dimerization and results in a greater purple coloration of the solution at lower temperatures as compared to a bluish color at room temperature.

Figure 7:
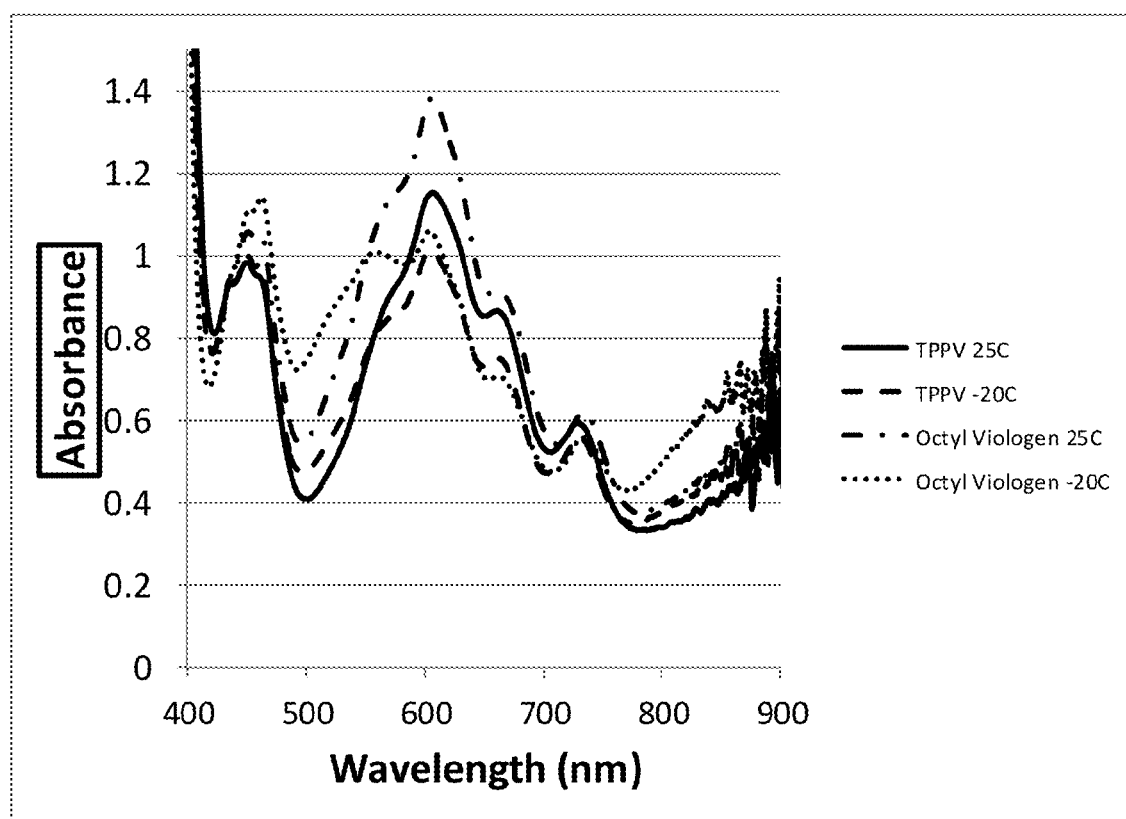
FIG. 7 provides a UV-Vis absorption spectra illustrating the change in color of an electrochromic window made with 30 mM 1,1'-dioctyl-4,4'-bipyridinium bis(tetrafluoroborate) ("1,1'-dioctyl viologen") and 30 mM 5,10-di-hydro-5,10-dimethyl phenazine with a cell spacing of 90 μm in comparison to an identical part made with 30 mM 4,4'-[3-(triphenylphosphonium)propyl]-1,1'-dipyridinium tetra(tetrafluoroborate) ("TPPV") instead of 1,1'-dioctyl viologen, according to the examples.
Figure 8:
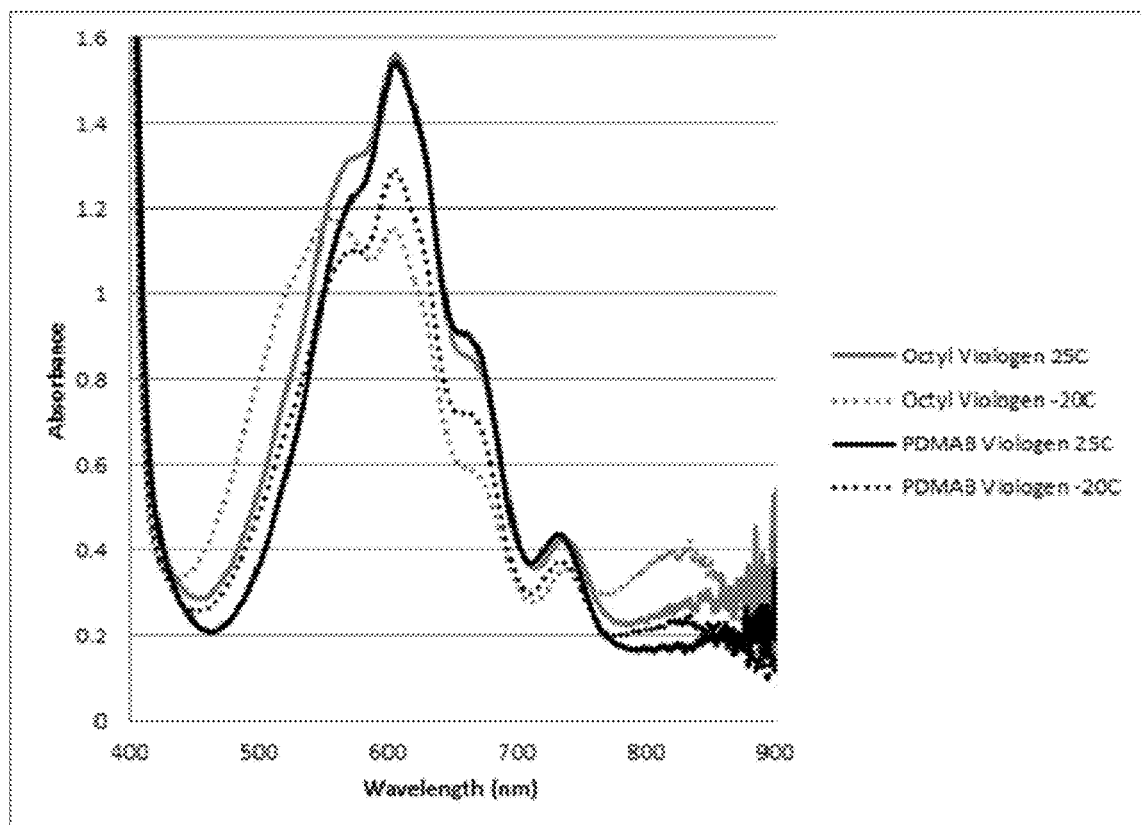
FIG. 8 provides a UV-Vis absorption spectra comparing an electrochromic window made with 30 mM 1,1'-dioctyl viologen and 30 mM 5,10-di-hydro-5,10-dimethyl phenazine with a cell spacing of 90 μm with an identical part made with 30 mM propanoldimethylammoniumbutyl viologen bis(tetrafluoroborate) ("PDMAB") instead of 1,1'-dioctyl viologen, according to the examples.

The advantage of the compounds disclosed herein can be further seen in the change in color of an electrochromic window made with 30 mM dioctylviologen bis(tetrafluoroborate) and 30 mM 5,10-di-hydro-5,10-dimethyl phenazine with a cell spacing of 90 μm compared to an identical part made with 30 mM TPPV from Example 6, as illustrated in FIG. 7. The EC element made with the dioctylviologen exhibited a color change (ΔE) of 26.25 nm compared to a ΔE of 13.15 nm for the part made with TPPV. FIG. 8 similarly compares an electrochromic window made with 30 mM dioctylviologen bis(tetrafluoroborate) and 30 mM 5,10-di-hydro-5,10-dimethyl phenazine with a cell spacing of 90 μm compared to an identical part made with 30 mM propanoldimethylammoniumbutyl viologen ("PDMAB") from Example 7.

Colorations of red-violet ($\lambda_{max}$=530 or 560 nm), blue ($\lambda$max=600 nm) and light purple ($\lambda_{max}$=560 and 600 nm) are observed in the various viologens and their derivatives. Generally the red-violet color is recognized as the dimer of the reduced viologen, the blue color is the color of a viologen radical and the light purple color is attributed to the mixed color of the monomer and the dimer. As can be understood by the UV Spectrometry results, the non-dimerizing electrochromic compounds described herein exhibit a $\lambda_{max}$ of about 600-630 nm or greater (e.g., FIGS. 5-6), whereas viologens capable of dimerization exhibit two large absorptions at both 540-550 nm (e.g., FIGS. 5-6) and 600-620 nm, which indicates the presence of a dimer and monomer. The non-dimerizing electrochromic compounds described herein serve to prevent the color produced as a result of the formation of dimers by viologen compounds lacking the structure of the compounds described herein. Therefore the compounds disclosed herein have great utility in various electrochromic devices, particularly in the area of surface-confined electrochromic materials.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An electrochromic device comprising:
   a non-dimerizing electrochromic compound represented by Formula (I):

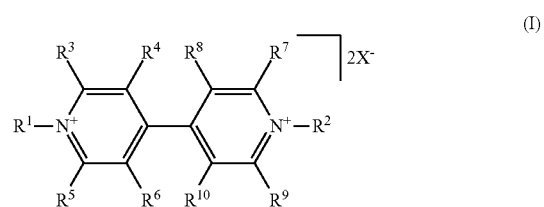

wherein:
   $R^1$ and $R^2$ are individually alkyl, siloxyalkyl, hydroxyalkyl, alkenyl, or aralkyl;
   $R^4$, $R^6$, $R^8$, and $R^{10}$ are individually H, $OR^{20}$, F, Cl, Br, I, CN, $NO_2$, alkyl, or aryl;
   $R^3$ and $R^5$ are individually secondary alkyl, tertiary alkyl, or a group of Formula (II):

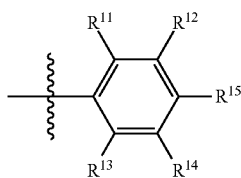

(II)

wherein:
R$^{11}$, R$^{12}$, R$^{13}$, and R$^{14}$ are individually H, OR$^{20}$, F, Cl, Br, I, CN, NO$_2$, or alkyl;
R$^{15}$ is OH, F, Cl, Br, I, CN, NO$_2$, —OC(O)NR$^{16}$R$^{17}$, Et, Pr, iso-propyl, butyl, sec-butyl, tert-butyl, alkoxy, or OC(O)NH(CH$_2$)$_n$COOH;
R$^{16}$ is H or alkyl; and
R$^{17}$ is H, methyl, ethyl, propyl, iso-propyl, butyl, sec-butyl, tert-butyl, or —(CH$_2$)$_n$Si(OR$^{18}$)$_3$;
R$^{18}$ is H or alkyl; and
n is 1 to 10;
R$^7$ and R$^9$ are H;
R$^{20}$ is H or alkyl; and
X is an anion.

2. The electrochromic device of claim 1, wherein R$^{11}$, R$^{12}$, R$^{13}$, and R$^{14}$ are individually H or alkyl.

3. The electrochromic device of claim 1, wherein R$^{11}$, R$^{12}$, R$^{13}$, and R$^{14}$ are H, and R$^{15}$ is methoxy, ethoxy, propoxy, ethyl, propyl, iso-propyl, butyl, sec-butyl, or tert-butyl.

4. The electrochromic device of claim 1, wherein R$^{17}$ is alkyl or siloxy alkyl.

5. The electrochromic device of claim 1, wherein R$^1$ and R$^2$ are individually aralkyl, C$_1$-C$_{12}$ alkyl or C$_1$-C$_{12}$ hydroxyalkyl.

6. An electrochromic device comprising:
a non-dimerizing electrochromic compound represented by Formula (III):

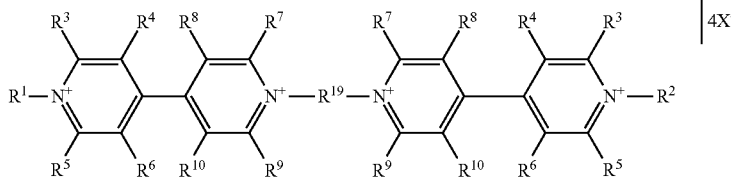

(III)

wherein:
R$^1$ and R$^2$ are individually alkyl, siloxyalkyl, hydroxyalkyl, alkenyl, or aralkyl;
R$^4$, R$^6$, R$^8$, and R$^{10}$ are individually H, OR$^{20}$, F, Cl, Br, I, CN, NO$_2$, alkyl, or aryl;
R$^3$ and R$^5$ are individually secondary alkyl, tertiary alkyl, or a group of Formula (II):

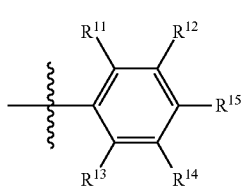

(II)

wherein:
R$^{11}$, R$^{12}$, R$^{13}$, and R$^{14}$ are individually H, OR$^{20}$, F, Cl, Br, I, CN, NO$_2$, or alkyl;
R$^{15}$ is OH, F, Cl, Br, I, CN, NO$_2$, —OC(O)NR$^{16}$R$^{17}$, Et, Pr, iso-propyl, butyl, sec-butyl, tert-butyl, alkoxy, or OC(O)NH(CH$_2$)$_n$COOH;
R$^{16}$ is H or alkyl; and
R$^{17}$ is H, methyl, ethyl, propyl, iso-propyl, butyl, sec-butyl, tert-butyl, or —(CH$_2$)$_n$Si(OR$^{18}$)$_3$;
R$^{18}$ is H or alkyl; and
n is 1 to 10;
R$^7$ and R$^9$ are H;
R$^{19}$ is (CH$_2$)$_{n'}$ or arylene, and n' is from 1 to 12;
R$^{20}$ is H or alkyl; and
X is an anion.

7. The electrochromic device of claim 6, wherein R$^{19}$ is (CH$_2$)$_{3-8}$ or 1,4-phenylene.

8. The electrochromic device of claim 1, wherein R$^4$, R$^6$, R$^8$, and R$^{10}$ are individually H, OH, or alkyl.

9. The electrochromic device of claim 1, wherein X$^-$ is F$^-$, Cl$^-$, Br$^-$, I$^-$, BF$_4^-$, PF$_6^-$, SbF$_6^-$, AsF$_6^-$, ClO$_4^-$, SO$_3$CF$_3^-$, N(CN)$_2^-$, N(CF$_3$SO$_2$)$_2^-$, C(CF$_3$SO$_2$)$_3^-$, N(SO$_2$C$_2$F$_5$)$_2^-$, $^-$Al(OC(CF$_3$)$_3$)$_4$ or $^-$BAr$_4$, wherein Ar is a aryl or fluorinated aryl group.

10. The electrochromic device of claim 1 further comprising:
an electrochromic medium comprising the non-dimerizing electrochromic compound; and
a chamber defined by a first conductive surface of first substrate, a second conductive surface of a second substrate, and a sealing member joining the first substrate to the second substrate,
wherein the electrochromic medium is disposed within the chamber.

11. The electrochromic device of claim 10 further comprising an anodic component and a solvent.

12. The electrochromic device of claim 1, wherein R$^3$ and R$^5$ are each a group of Formula (II) and R$^{15}$ is —OC(O)NR$^{16}$R$^{17}$.

13. The electrochromic device of claim 1, wherein R$^{15}$ is OC(O)NH(CH$_2$)—Si(OEt)$_3$.

14. The electrochromic device of claim 1, wherein R$^3$ and R$^5$ are each a group of Formula (II) and R$^{15}$ is OC(O)NH(CH$_2$)$_n$Si(OEt)$_3$.

* * * * *